US00RE41148E

(19) United States
(12) Reissued Patent
Burnside et al.

(10) Patent Number: US RE41,148 E
(45) Date of Reissued Patent: Feb. 23, 2010

(54) ORAL PULSED DOSE DRUG DELIVERY SYSTEM

(75) Inventors: Beth A. Burnside, Bethesda, MD (US); Xiaodi Guo, Apex, NC (US); Kimberly Fiske, Downingtown, PA (US); Richard A. Couch, Bryn Mawr, PA (US); Donald J. Treacy, Woodbine, MD (US); Rong-Kun Chang, Rockville, MD (US); Edward M. Rudnic, North Potomac, MD (US); Charlotte M. McGuinness, Bethesda, MD (US)

(73) Assignee: Shire Laboratories, Inc., Rockville, MD (US)

(21) Appl. No.: 11/091,010

(22) PCT Filed: Oct. 20, 1999

(86) PCT No.: PCT/US99/24554

§ 371 (c)(1),
(2), (4) Date: Jul. 19, 2001

(87) PCT Pub. No.: WO00/23055

PCT Pub. Date: Apr. 27, 2000

Related U.S. Patent Documents

Reissue of:
(64) Patent No.: 6,605,300
Issued: Aug. 12, 2003
Appl. No.: 09/807,462
Filed: Jul. 19, 2001

U.S. Applications:
(63) Continuation-in-part of application No. 09/176,542, filed on Oct. 21, 1998, now Pat. No. 6,322,819.

(51) Int. Cl.
*A61K 9/48* (2006.01)
*A61K 9/24* (2006.01)
*A61K 9/26* (2006.01)
*A61K 31/135* (2006.01)

(52) U.S. Cl. ..... 424/452; 424/458; 424/468; 424/469; 424/470; 424/471; 424/472; 514/649

(58) Field of Classification Search ..... 424/452, 424/458, 468–472, 514, 649
See application file for complete search history.

(56) References Cited

U.S. PATENT DOCUMENTS 2,099,402 A 11/1937 Keller (Continued)

FOREIGN PATENT DOCUMENTS

AU 109438 1/1940

(Continued)

OTHER PUBLICATIONS

US 6,034,101, 3/2000, Gupta et al. (withdrawn)
Complaint for Declaratory Judgment, *Impax Laboratories, Inc.* v. *Shire International Laboratories, Inc.* (Civ. Action No. 05772) and Exhibits attached thereto.

(Continued)

*Primary Examiner*—Shengjun Wang
(74) *Attorney, Agent, or Firm*—McDermott Will & Emery LLP

(57) ABSTRACT

A multiple pulsed dose drug delivery system for pharmaceutically active amphetamine salts, comprising an immediate-release component and an enteric delayed-release component wherein (1) the enteric release coating has a defined minimum thickness and/or (2) there is a protective layer between the pharmaceutically active amphetamine salt and the enteric release coating and/or (3) there is a protective layer over the enteric release coating. The product can be composed of either one or a number of beads in a dosage form, including either capsule, tablet, or sachet method for administering the beads.

20 Claims, 7 Drawing Sheets

U.S. PATENT DOCUMENTS

| | | | | | |
|---|---|---|---|---|---|
| 2,738,303 | A | | 3/1956 | Blythe | |
| 3,048,526 | A | | 8/1962 | Boswell | |
| 3,365,365 | A | | 1/1968 | Butler et al. | |
| 3,979,349 | A | | 9/1976 | Fink | |
| 4,049,791 | A | | 9/1977 | Cohen | |
| 4,723,958 | A | * | 2/1988 | Pope et al. | 604/890.1 |
| 4,728,512 | A | | 3/1988 | Mehta et al. | |
| 4,765,989 | A | * | 8/1988 | Wong et al. | 424/473 |
| 4,794,001 | A | | 12/1988 | Mehta et al. | |
| 4,871,549 | A | * | 10/1989 | Veda et al. | 424/494 |
| 4,891,230 | A | * | 1/1990 | Geoghegan et al. | 424/461 |
| 4,894,240 | A | * | 1/1990 | Geoghegan et al. | 424/497 |
| 4,902,516 | A | * | 2/1990 | Korsatko et al. | 424/497 |
| 4,917,899 | A | * | 4/1990 | Geoghegan et al. | 424/461 |
| 5,002,776 | A | * | 3/1991 | Geoghegan et al. | 424/497 |
| 5,011,692 | A | * | 4/1991 | Fujioka et al. | 424/426 |
| 5,011,694 | A | * | 4/1991 | Nuernberg et al. | 424/464 |
| 5,051,262 | A | * | 9/1991 | Panoz et al. | 424/468 |
| 5,093,200 | A | * | 3/1992 | Watanabe et al. | 428/407 |
| 5,137,733 | A | | 8/1992 | Noda et al. | |
| 5,202,159 | A | | 4/1993 | Chen et al. | |
| 5,226,902 | A | * | 7/1993 | Bae et al. | 604/892.1 |
| 5,229,131 | A | * | 7/1993 | Amidon et al. | 424/451 |
| 5,260,068 | A | | 11/1993 | Chen | |
| 5,260,069 | A | | 11/1993 | Chen | |
| 5,275,819 | A | * | 1/1994 | Amer et al. | 424/408 |
| 5,312,388 | A | * | 5/1994 | Wong et al. | 604/892.1 |
| 5,364,620 | A | * | 11/1994 | Geoghegan et al. | 424/497 |
| 5,378,474 | A | | 1/1995 | Morella et al. | |
| 5,395,628 | A | * | 3/1995 | Noda et al. | 424/490 |
| 5,407,686 | A | * | 4/1995 | Patel et al. | 424/468 |
| 5,411,745 | A | | 5/1995 | Oshlack et al. | |
| 5,422,121 | A | | 6/1995 | Lehmann et al. | |
| 5,474,786 | A | * | 12/1995 | Kotwal et al. | 424/472 |
| 5,496,561 | A | | 3/1996 | Okada et al. | |
| 5,541,170 | A | | 7/1996 | Rhodes et al. | |
| 5,616,345 | A | * | 4/1997 | Geoghegan et al. | 424/497 |
| 5,618,559 | A | | 4/1997 | Desai et al. | |
| 5,733,575 | A | | 3/1998 | Mehra et al. | |
| 5,800,836 | A | * | 9/1998 | Morella et al. | 424/489 |
| 5,824,341 | A | * | 10/1998 | Seth et al. | 424/473 |
| 5,824,342 | A | * | 10/1998 | Cherukuri et al. | 424/484 |
| 5,824,343 | A | * | 10/1998 | Ng et al. | 424/486 |
| 5,837,284 | A | * | 11/1998 | Mehta et al. | 424/459 |
| 5,840,329 | A | * | 11/1998 | Bai | 424/458 |
| 5,885,616 | A | * | 3/1999 | Hsiao et al. | 424/472 |
| 5,885,998 | A | * | 3/1999 | Bencherif et al. | 514/256 |
| 5,891,474 | A | * | 4/1999 | Busetti et al. | 424/490 |
| 6,322,819 | B1 | | 11/2001 | Burnside et al. | |
| 6,605,300 | B1 | | 8/2003 | Burnside et al. | |
| 6,749,867 | B2 | | 6/2004 | Robinson et al. | |
| 6,764,696 | B2 | | 7/2004 | Pather et al. | |
| 2004/0059002 | A1 | | 3/2004 | Couch et al. | |

FOREIGN PATENT DOCUMENTS

| | | | |
|---|---|---|---|
| EP | 640 337 | | 3/1995 |
| JP | 59-082311 | | 5/1984 |
| JP | 03-148215 | | 6/1991 |
| JP | 07-061922 | | 3/1995 |
| JP | 09-249557 | | 9/1997 |
| JP | 09-267035 | | 10/1997 |
| JP | 10-081634 | | 3/1998 |
| WO | WO87/00044 | * | 1/1987 |
| WO | WO90/09168 | * | 8/1990 |
| WO | WO-97/03673 | | 2/1997 |
| WO | WO-98/14168 | | 4/1998 |
| WO | WO-99/03471 A | | 1/1999 |
| WO | WO-00/25752 A | | 5/2000 |
| WO | WO-00/35450 A | | 6/2000 |

OTHER PUBLICATIONS

Fukumori, Coating of Multiparticulates Using Polymeric Dispersions, Multiparticulate Oral Drug Delivery (Swarbrick and Selassie eds. 1994), 79–110.

Bodmeier et al., The Influence of Buffer Species and Strength on Dittiazem HCl Release from Beads Coated with the Aqueous Cationic Polmer Dispersions, Eudraglt RS, RL 30D, Pharmaceutical Research vol. 13, No. 1, 1996, 52–56.

Shire Laboratories Inc.'s Opposition to Barr Laboratories' Motion to Amend Its Answers and Counterclaims, Sep. 15, 2004.

Chan, Materials Used for Effective Sustained–Release Products, Proceedings of the International Symposium held on Jan. 29–31, 1987 (The Bombay College of Pharmacy 1988), 69–84.

PDR Drug Information for Ritalin LA Capsules, Apr. (2004).

Greenhill et al., A Pharmacokinetic/Pharmacodynamic Study Comparing a Single Morning Dose of Adderall to Twice–Daily Dosing in Children with ADHD. J. Am. Acad. Adolesc. Psychiatry, 42:10, Oct. 2003.

Teva Notice letter: Feb. 21, 2005.

Bauer, et al., Cellulose Acetate Phthalate (CAP) and Trimellitate (CAT), Coated Pharmaceutical Dosage Forms (1998), 102–104.

Guidance for Industry: SUPAC–MR: Modified Release Solid Oral Dosage Forms (1997).

Treatise on Controlled Drug Delivery, pp. 285–299 (Agis Kydonieus ed. 1992).

Guidance for Industry: Extended Release Oral Dosage Forms: Development, Evaluation, and Application of In Vitro/In Vivo Correlations (1997).

Wouessidjewe, Aqueous polymethacrylate Dispersions as Coating Materials for Sustained and Enteric Release Systems, S.T.P. Pharma Sciences 7(6) 469–475 (1997).

Adderall XR Package Inset, Sep. (2004).

Marcotte et al., Kinetics of Protein Diffusion from a Poly(D, L–Lactide) Reservoir System, Journal of Pharmaceutical Sciences, vol. 79, No. 5, May 1990.

Guo Deposition Transcript, Jan. 24, 2005.

Watano, et al., Evaluation of Aqueous Enteric Coated Granules prepared by Moisture Control Method in Tumbling Fluidized Bed Process, Chem. Pharm. Bull. 42(3) 663–667 (1994).

Schaffer Deposition Transcript, Aug. 17, 2005.

Rambali, et al., Using experimental design to optimize the process parameters in fluidized bed granulation on a semi–full scale, International Journal of Pharmaceutics 220 (2001) 149–160.

Treacy Deposition Transcript, Aug. 31, 2004.

Tulloch, et al., SL1381 (Adderall XR), a Two–component, Extended–Release Formulation of Mixed Amphetamine Salts: Bioavailability of Three Test formulatons and Comparison of Fasted, Fed, and Sprinkled Administration, PHARMACOTHERAPY vol. 22, No. 11. (2002), 1405–1415.

Chang Deposition Transcript, Sep. 8, 2004.

Edward Stempel, Prolonged Drug Action, HUSA's Pharmaceutical Dispensing, Sixth Edition, 1966, 464, 481–485.

McGuiness Deposition Transcript, Aug. 6, 2004.

Remington's Pharmaceutical Sciences, RPS XIV, 1700–1714.

Fiske Deposition Transcript, Sep. 17, 2004.

Vasilevska, et al., Preparation and Dissolution Characteristics of Controlled Release Diltiazem Pellets, Drug Development and Industrial Pharmacy, 18(15), 1649–1661 (1992).

Opening Expert Report of Dr. Walter Chambliss and exhibits thereto, Mar. 15, 2005.

Agyilirah GA and Bauker SB, Polymers for Enteric Coating Applications, Polymers for Controlled Drug Delivery (Peter J. Tarcha ed. 1991) 39–66.

Impax Laboratories, Inc.'s First Amended Answer and Affirmative Defenses.

Moller, Dissolution Testing of Delayed Release Preparations, Proceedings of the International Symposium held on Jan. 29–31, 1987 (The Bombay College of Pharmacy 1988), 85–111.

Impax Laboratories, Inc.'s Reply Memorandum in Support of the Motion to Amend its Answer dated Mar. 18, 2005 and exhibits thereto.

Stevens, et al., Controlled, Multidose, Pharmacokinetic Evaluation of Two Extended–Release Carbamazepine Formulations (Carbatrol and Tegretol–XR), Journal of Pharmaceutical Sciences vol. 87, No. 12, Dec. 1998, 1531–1534.

Deposition transcript of Honorable Gerald J. Mossinghoff and exhibits thereto.

Physicians' Desk Reference: Adderall, 51st Ed. (1997).

Expert Report of Dr. Joseph R. Robinson and exhibits thereto, Feb. 28, 2005.

Sriamornsak, et al., Development of sustained release theophylline pellets coated with calcium pectinate, Journal of Controlled Release 47 (1997) 221–232.

Answering Expert Report of Dr. Alexander Klibanov, Apr. 25, 2005.

Sprowls' American Pharmacy: An Introduction to Pharmaceutical Techniques and Dosage Forms, 7th Ed. (1974), 387–388.

Barr Laboratories' Objections and Responses to Plaintiff Shire Laboratories Inc.'s Fifth Set of Interrogatories (No. 17).

Sheen, et al., Aqueous Film Coating Studies of Sustained Release Nicotinic Acid Pellets: An In–Vitro Evaluation, Drug Development and Industrial Pharmacy, 18(8), 851–860 (1992).

Barr Laboratories' Objections and Responses to Plaintiff Shire Laboratories Inc.s' Fourth Set of Interrogatories (Nos. 15–16).

Barr Laboratories' Inc.'s Objections and Responses to Shire laboratories Inc.'s Second Set of Interrogatories (Nos. 8–11).

Scheiffele, et al., Studies Comparing Kollicoat MAE 30 D with Commercial Cellulose Derivatives for Enteric Coating on Caffeine Cores, Drug Development and Industrial Pharmacy, 24(9), 807–818 (1998), 807–818.

The United States Pharmacopeia 27, National Formulary 22 (2004) pp. 2302–2312.

Expert Report of the Honorable Gerald J. Mossinghoff and exhibits thereto, Mar. 16, 2005.

The United States Pharmacopeia 23, National Formulary 18 (1995) pp. 1791–1799.

Charles S.L. Chiao and Joseph R. Robinson, Sustained–Release Drug Delivery Systems, Remington: The Science and Practice of Pharmacy, Tenth Edition (1995) 1660–1675.

The Merck Index: Amphetamine, 12th Ed., 620.

Couch Deposition Transcript, Sep. 14, 2004.

Shargel;. Pharmacokinetics of Oral Absorption, Applied Biopharmaceutics & Pharmacokinetics. 5th Ed. (2005), 164–166.

American Chemical Society, Polymer Preprints, pp. 633–634, vol. 34, No. 1, Mar. 1993.

Remington: The Science and Practice of Pharmacy, Elutriation, 20th Ed. (2000), 690.

Harrington Deposition Transcript, Jul. 27, 2005.

Physicians' Desk Reference: Ritalin, 56th Ed. (2002).

Kennerly S. Patrick & John S. Markowitz, Pharmacology of Methylphenidate, Amphetamine Enantiomers and Permoline in Attention–Deficit Hyperactivity Disorder, Human Psychopharmacology, vol. 12, 527–546 (1997).

Physicians' Desk Reference: Adderall, 56th Ed. (2002).

Guidance for Industry: Food–Effect Bioavailability and Fed Bioequivalence Studies (2002).

McGraw–Hill Dictionary of Scientific and Technical Terms, 5th Ed. (1994), 97, 972.

McGough et al., Pharmacokinetics of SL1381 (Adderall XR), an Extended–Release Formulation of Adderall, Journal of the American Academy of Child & Adolescent Psychiatry, vol. 42, No. 6, Jun. 2003.

Handbook of Pharmaceutical Excipients: Ethylcellulose, Polymethacrylates, (4th ed. (2003), 237–240, 462–468.

Mathir et al., In vitro characterization of a controlled–release chlorpheniramine maleate delivery system prepared by the air–suspension technique, J. Microencapsulaton, vol. 14, No. 6, 743–751 (1997).

R. Bianchini & C. Vecchio, Oral Controlled Release Optimization of Pellets Prepared by Extrusion–Spheronization Processing, IL Farmaco 44(6), 645–654, 1989.

Chang et al., Preparation and Evaluation of Shellac Pseudolatex as an Aqueous Enteric Coating Systems for Pellets, International Journal of Pharmaceuticals, 60 (1990) 171–173, 1990.

Garnett et al., Pharmacokinetic Evaluation of Twice–Daily Extended–Release Carbamazepine (CBZ) and Four–Times–Daily Immediate–Release CBZ in Patients with Epilepsy, Epilepsia 39(3):274–279, 1998.

Liu et al., Comparative Release of Phenylprepanolamine HCl from Long–Acting Appetite Suppressant Product: Acutrim vs. Dexatrim, Drug Development and Industrial Pharmacy, 10(10), 1639–1661 (1984).

Krowczynski & Brozyna, Extended–Release Dosage Forms, pp. 123–131 (1987).

C. Lin et al., Bioavailability of d–pseudoephedrine and Azatadine from a Repeat Action Tablet Formulation, J Int Med Res (1982), 122–125.

Rosen et al., Absorption and Excretion of Radioactively Tagged Dextroamphetamine Sulfate from a Sustained–Release Preparation, Jama, vol. 194, No. 11, Dec. 13, 1965. 145–147.

C. Lin et al., Compartive Bioavailability of d–pseudoephedrine from a Conventional d–pseudoephedrine Sulfate Tablet and from a Repeat Action Tablet, J Int Med Res (1982) 10, 126–128.

Pelham et al., A Comparison of Morning–Only and Morning/Late Afternoon Adderall to Morning–Only, Twice–Daily, and Three Times–Daily Methylphenidate in Children with Attention–Deficit/Hyperactivity Disorder, Pediatrics, vol. 104, No. 6, Dec. 1999.

Serajuddin, et al., Selection of Solid Dosage Form Composition through Drug–Excipient Compatibility Testing, Journal of Pharmaceutical Sciences vol. 88, No. 7, Jul. 1999, 696–704.

Slattum, et al., Comparison of Methods for the Assessment of Central Nervous System Stimulant Response after Dextroamphetamine Adminstration to Healthy Male Volunteers, J. Clin Pharmacol 1996; 36: 1039–1050.

Lin & Cheng, In–vitro Dissolution Behaviour of Spansule–type Micropellets Prepared by Pan Coating Method, Pharm. Ind. 51 No. 5 (1989).

Remington's Pharmaceutical Sciences, Fifteenth Edition (1975) 1624–1625.

Ansel et al., Rate Controlled Dosage Forms and Drug Delivery Systems, Pharmaceutical Dosage Forms and Drug Delivery Systems, 6th Ed. (1995), 213–222.

Chan, New Polymers for Controlled Release Products, Controlled Release Dosage Forms Proceedings of the International Symposium held on Jan. 29–31, 1987 (The Bombay College of Pharmacy 1988) 59–111.

Leopold & Eikeler, Eudragit E as Coating Material for the pH–Controlled Drug Release in the Topical Treatment of Inflammatory Bowel Disease (IBD), Journal of Drug Targeting, 1998, vol. 6, No. 2, pp. 85–94.

Jarowski, The Pharmaceutical Pilot Plant, Pharmaceutical Dosage Forms: Tablets, vol. 3, 2nd Ed. (1990), 303–367.

Remington: The Science and Practice of Pharmacy, Basic Pharmacokinetics, 16th Ed. (1980), 693.

Rong–Kun Chang and Joseph R. Robinson, Sustained Drug Release from Tablets and Particles Through Coating, Pharmaceutical Dosage Forms: Tablets (Marcel Dekker, Inc. 1990), 199–302.

Hall HS and Pondell RE, Controlled Release Technologies: Methods, Theory, and Applications, pp. 133–154 (Agis F. Kydonieus ed. 1980).

Porter and Bruno Coating of Pharmaceutical Solid–Dosage Forms, 77–160.

Barr Laboratores' Memorandum In Support of its Motion to Amend its Pleadings and exhibits thereto.

Answering Expert Report of Robert Langer, Apr. 25, 2005.

Hans–Martin Klein & Rolf W. Gunther, Double Contrast Small Bowel Follow–Through with an Acid–Resistant Effervescent Agent, Investigative Radiology vol. 28, Jul. 1993.

Opening Expert Report of Dr. Michael Mayersohn and exhibits thereto, Mar. 12, 2005.

Rudnic Deposition Transcript, Jul. 28, 2004.

Burnside Deposition Transcript, Feb. 2, 2005.

Kao et al., Lag Time Method to Delay Drug Release to Various Sites in the Gastrointestinal Tract, Journal of Controlled Release 44(1997) 263–270.

Freedom of Information Request Results for—Dexadrine (SmithKline Beecham): May 20, 1976 Disclosable Approval Information.

Teva Notice letter: Jun. 1, 2005.

Prescribing Information: Dexedrine, brand of dextroamphetamine sulfate (2001).

Husson et al., Influence of Size Polydispersity on Drug Release from Coated Pellets, International Journal of Pharmaceutics, 86 (1992) 113–121, 1992.

Rong–Kun Chang et al., Formulation Approaches for Oral Pulsatile Drug Delivery, American Pharmaceutical Review.

Kiriyama et al., The Bioavailability of Oral Dosage Forms of a New HIV–1 Protease Inhibitor, KNI–272, in Beagle Dogs, Biopharmaceutics & Drug Disposition, vol. 17 125–134 (1996).

Klaus Lehmann, Coating of Multiparticulates Using Polymeric Solutions, Multiparticulate Oral Drug Delivery (Swarbrick and Sellassie ed., 1994).

Goodhart et al., An Evaluation of Aqueous Film–forming Dispersions for Controlled Release, Pharmaceutical Technology, Apr. 1984.

Rosen, et al., Absorption and Excretion of Radioactively Tagged Dextroamphetamine Sulfate From a Sustained–Release Preparation, Journal of the American Medical Association, Dec. 13, 1965, vol. 194, No. 11, 1203–1205.

Leon Lachman, Herbert A. Lieberman, Joseph L. Kanig, The Theory and Practice of Industrial Pharmacy, Second Edition (1976) 371–373.

Wesdyk, et al., Factors affecting differences in film thickness of beads coated in fluidized bed units, International Journal of Pharmaceutics, 93 101–109, (1993).

Daynes, Treatment of Noctural Enuresis with Enteric–Coated Amphetamine, The Practitioner, No. 1037, vol. 173, Nov. 1954.

Physicians' Desk Reference: Dexedrine 56th Ed. (2002).

The United States Pharmacopeia 26, National Formulary 21 (2003) pp. 2157–2165.

Barr Laboratories' Supplemental Objections and Responses to Plaintiff Shire Laboratories Inc.'s Third Set of Interrogatories (Nos. 12–14 Redacted).

Rong–Kun Chang, A Comparison of Rheological and Enteric Properties among Organic Solutions, Ammonium Salt Aqueous Solutions, and Latex Systems of Some Enteric Polymers, Pharmaceutical Technology, Oct. 1990.

Guo Deposition Transcript, Jul. 26, 2004.

Chang Deposition Transcript, Jan. 20, 2005.

Holt, Bioequivalence Studies of Ketoprofen: Product formulation, Pharmacokinetics, Deconvolution, and In Vitro – In Vivo correlations, Thesis submitted to Oregon State University, Aug. (1997).

Cody et al., Amphetamine Enantiomer Excretion Profile Following Administration of Adderall, Journal of Analytical Toxicology, vol. 2, Oct. 2003, 485–492.

Ishibashi et al., Design and Evaluatin of a New Capsule–type Dosage Form for Colon–Targeted Delivery of Drugs, International Journal of Pharmaceutics 168, (1998) 31–40, 1998.

Harris et al., Aqueous Polymeric Coating for Modified–Release Pellets, Acqueous Polymeric Coating for Pharmaceutical Dosage Forms (McGinity ed., 1989).

J. Sjogren, Controlled release oral formulation technology, Rate Control in Drug Therapy, (1985) 38–47.

Burns et al., A Study of Enteric–coated Liquid–filled Hard Gelatin Capsules with Biphasic Release Characteristics, International Journal of Pharmaceutics 110 (1994) 291–296.

The Merck Index: Amphetamine, 13th Ed. (2001), 97, 1089.

Impax Laboratories, Inc.'s First Supplemental Responses to Shire Laboratories Inc.'s First Set of Interrogatories (Nos. 11–12).

Burnside Deposition Transcript, Feb. 3, 2005.

Brown et al., Plasma Levels of d–Amphetamine in Hyperactive Children, Psychopharmacology 62, 133–140, 1979.

Mehta et al., Evaluation of Fluid–bed Processes for Enteric Coating Systems, Pharmaceutical Technology, Apr. 1986.

Handbook of Pharmaceutical Excipients: Plymethacrylates, (2nd ed. 1994), 361–366.
Impax Laboratories, Inc.'s Memorandum in Support of the Motion to Amend its Answer dated Feb. 25, 2005 and exhibits thereto.
Brauer et al., Acute Tolerance to Subjective but not Cardiovascular Effects of d–Amphetamine in Normal, Healthy Men, Journal of Clinical Psychopharmacology, 1996; 16(1):72–76.
Glatt, The World of the Fluid Bed, Fluid Bed Systemsm, 1–19.
Brown et al., Behavior and Motor Activity Response in Hyperactive Children and Plasma Amphetamine Levels Following a Sustained Release Preparation, Journal of the American Academy of Child Psychiatry, 19:225–239, 1980.
Office Action mailed Mar. 2, 2005 in European Patent Aplication No. 99 970594.0–2123.
Angrist et al., Early Pharmacokinetics and Clinical Effects of Oral D–Amphetamine in Normal Subjects, Biol. Psychiatry 1987, 22: 1357–1368.
Court Docket for *Shire Laboratories* v. *Teva Pharmaceutical Industries Ltd.*, Case No. 2:06–cv–00952–SD, Jan. 8, 2007.
Complaint in *Shire Laboratories* v. *Teva Pharmaceutical Industries Ltd.*, and exhibits thereto, Case No. 2:06–cv–00952–SD, Mar. 2, 2006.
Answer and Counterclaims in *Shire Laboratories* v. *Teva Pharmaceutical Industries Ltd.*, Case No. 2:06–cv–00952–SD, Jul. 24, 2006.
Reply to Counterclaims in *Shire Laboratories* v *Teva Pharmaceutical Industries Ltd.*, Case No. 2:06–cv–00952–SD, Aug. 16, 2006.
Defendants' Response to Plaintiff Shire's First Set of Interrogatories (1–12) in *Shire Labatories* v. *Teva Pharmaceutical Industries Ltd.*, Case No. 2:06–cv–00952–SD, Sep. 20, 2006.
Defendants' Responses to Plaintiff's First Set of Request for the Production of Documents and Things (1–70) in *Shire Laboratories* v. *Teva Pharmaceutical Industries Ltd.*, Case No. 2:06–cv–00952–SD, Oct. 4, 2006.
Plaintiff's Response to Defendants' First Set of Interrogatories in *Shire Labatories* v. *Teva Pharmaceutical Industries Ltd.*, Case No. 2:06–cv–00952–SD, Oct. 11, 2006.
Plaintiff's Response to Defendants' First Set of Production Requests in *Shire Laboratories* v. *Teva Pharmaceutical Industries Ltd.*, Case No. 2:06–cv–00952–SD, Oct. 11, 2006.
Defendants' Responses to Plaintiff's Second Set of Requests for the Production of Documents and Things (71–80) in *Shire Laboratories* v. *Teva Pharmaceuticals Industries Ltd.*, Case No. 2:06–cv–00952–SD, Nov. 8, 2006.
Defendants' Responses to Plaintiff Shire's Second Set of Interrogatories (No. 13) in *Shire Laboratories* v. *Teva Pharmaceuticals Industries Ltd.*, Case No. 2:06–cv–00952–SD, Nov. 8, 2006.
Petition Under Section 8 and exhibits thereto, submitted to the Canadian Patent Office on Dec. 4, 2006.
Exh. 3, Excerpts from the Deposition Transcript of Richard Chang, dated Sep. 8, 2004.
Exh. 4, Excerpts from the Deposition Transcript of Richard A. Couch, dated Sep. 14, 2004.
Exh. 5, Excerpts from the Deposition Transcript of Kimberly Fiske, dated Sep. 17, 2004.
Exh. 6, Excerpts from the Deposition Transcript of Charlotte M. McGuiness, dated Aug. 6, 2004.
Exh. 7, Excerpts from the Deposition Transcript of Beth Burnside, dated Feb. 2, 2005.
Exh. 8, Excerpts from the Deposition Transcript of Donald John Treacy, Jr., dated Aug. 31, 2004.
Exh. 9, Excerpts from the Deposition Transcript of Beth Burnside, dated Feb. 3, 2005.
Exh. 10, Excerpts from the Deposition Transcript of Xiaodi Guo, dated Jan. 24, 2005.
Exh. 11, Excerpts from the Deposition Transcript of Xiaodi Guo, dated Jul. 26, 2004.
Exh. 12, Excerpts from the Deposition Transcript of Edward Rudnic, dated Jul. 28, 2004.
Exh. 13, Excerpts from the Deposition Transcript of Richard Rong–Kun Chang, dated Jan. 20, 2005.
Exh. 14, Impax Laboratories Answer And Affirmative Defenses *Shire Laboratories, Inc.* v. *Impax Laboratories, Inc.*, Civil Action No. 03–CV–01164–GMS.
Exh. 15, Barr Laboratories' Amended Answer, Affirmative Defenses, And Counterclaims, *Shire Laboratories, Inc.* v. *Barr Laboratories, Inc.*, Civil Action No. 03–CV–6632–PKC.
Exh. 16, Barr Laboratories' Amended Answer, Affirmative Defenses And Counterclaims, *Shire Laboratories, Inc.* v. *Barr Laboratories, Inc.*, Civil Action No. 03–CV–1219–PKC.
Exh. 17, Reply to Barr Laboratories Inc.'s Amended Answer, Affirmative Defenses And Counterclaims, *Shire Laboratories, Inc.* v. *Barr Laboratories, Inc.*, Civil Action No. 03–CV–6632–PKC.
Exh. 18, Civil Docket For Case #: 1:03–cv–01164–GMS, *Shire Laboratories, Inc.* v. *Impax Laboratories, Inc.*, Civil Action No. 03–CV–01164–GMS.
Exh. 19, Civil Docket For Case #: 1:05–cv–00020–GMS, *Shire Laboratories, Inc.* v. *Impax Laboratories, Inc.*, Civil Action No. 05–20–GMS.
Exh. 20, Civil Docket For Case #: 1:03–cv–06632–VM–DFE, *Shire Laboratories, Inc.* v. *Barr Laboratories, Inc.*, Civil Action No. 03–CV–6632–PKC.
Exh. 21, Civil Docket For Case #: 1:03–cv–01219–PKC–DFE, *Shire Laboratories, Inc.* v. *Barr Laboratories, Inc.*, Civil Action No. 03–CV–1219–PKC.
Exh. 25, Barr Laboratories, Inc.'s '819 Notification Pursuant to § 505(j)(B)(ii) of the Federal Food, Drug and Cosmetic Act (21 U.S.C. § 355(j)(2)(B)(ii) and 21 C.F.R. § 314.95.
Exh. 26, Barr Laboratories, Inc.'s '300 Notification Pursuant to § 505(j)(2)(B)(ii) of the Federal Food, Drug and Cosmetic Act (21 U.S.C. § 355(j)(2)(B)(ii) and 21 C.F.R. § 314.95).
Exh. 27, Order Construing The Terms Of U.S. Patent Nos. 6,322,819 and 6,605,300, *Shire Laboratories, Inc.* v. *Impax Laboratories, Inc.*, Civil Action No. 03–CV–01164–GMS.
Gazzaniga, et al., *S.T.P. Pharma Sciences*, vol. 5, No. 1, gs. 83–88 (1995), Time dependent oral delivery for colon targeting.*
*Modern Pharmaceutics*, Banker, et al., eds., Marcel Dekker, Inc., New York, p. 350 (1996).*
Walia, et al., *Pharm. Dev. Tech.*, vol. 3, No. 1, pp. 103–113 (1998), Preliminary Evaluation of an Aqueous Wax Emulsion for Controlled–Release Coating.*
Wilding et al., *Pharmaceutical Research*, vol. 9, No. 5, pp. 654–657 (1992), Gastrointestinal Transit and Systemic Absorption of Captopil from Pulsed–Release Formulation.*
Xu, et al., *Pharmaceutical Research*, vol. 10, No. 8, pp. 1144–1152 (1993), Programmable Drug Delivery from an Erodible Association Polymer System.*

Conte, et al., *Biomaterials*, vol. 14, No. 13, pp. 1017–1023 (1993), Press–coated tablets for time–programmed release of drugs.*

Gazzaniga, et al., *Eur. J. Pharm. Biopharm.*, vol. 40, No. 4, pp. 246–250 (1994), Oral Chronotopic Drug Delivery System: Achievement of Time and/or Site Specificity.*

Pozzi, et al., *J. Controlled Release*, vol. 31, pp. 99–108 (1994), The Time Clock System: a new oral dosage form for fast and complete release of drug after a predetermined lag time.*

Snire Laboratory Inc's Complaint against Barr Laboratories based on Parent U.S. patent 6,322,815 in U S District Court for the Southern District of New York (Case No. 03–CV–1219(VM)(DFE)) 2003.*

Barr Laboratories' Answer. Affirmative Defenses and Counterclaim in Case No. 03–CV–1219(VM)(DFE) (S D N Y ) 2003.*

Barr's Paragraph IV Certification against Parent U S Patent 6,322,819 on Jan. 14, 2003.*

Transcript of Richard A. Couch 30(b)(6) Deposition in *Shire LLC* vs. *Sandoz Inc.* in the United States District Court for the District of Colorado, Dec. 14, 2007.

Transcript of Beth A. Burnside Deposition in *Shire LLC* vs. *Sandoz Inc.* in the United States District Court for the District of Colorado, Case No. 07–CV–00197–EWN–CBS, Nov. 30, 2007.

Transcript of Kimberly Fiske Farrand Deposition in *Shire, LLC* v. *Sandoz, Inc.* in Shire, LLC v. Sandoz, Inc. in the United States District Court for the District of Colorado, Dec. 4, 2007.

Defendant Sandoz, Inc.'s Answers and Objections to Plaintiff Shire LLC's Interrogatories (Nos. 1–9), in the United States District Court for the District of Colorado, Case No. 07–CV–00197–EWN–CBS, Jun. 18, 2007.

Defendant Sandoz, Inc.'s Answers and Objections to Plaintiff Shire LLC's Second Set of Interrogatories (Nos. 10–19), in the United States District Court for the District of Colorado, Case No. 07–CV–00197–EWN–CBS, Nov. 20, 2007.

Defendant Sandoz, Inc.'s Answers and Objections to Plaintiff Shire LLC's Third Set of Interrogatories (Nos. 20–25) and Supplement to Answers to Interrogatories 8 and 9, in the United States District Court for the District of Colorado, Case No. 07–CV–00197–EWN–CBS, Dec. 10, 2007.

Expert Report of Arthur J. Steiner in *Shire LLC* v. *Colony Pharmaceuticals, Inc.*, in the United States District Court for the District of Maryland, Case No. 1:07–cv–00718, Dec. 20, 2007.

Supplemental Expert Report of Harry G. Brittain, PhD, FRSC in *Shire LLC* v. *Colony Pharaceuticals, Inc.*, in the United States District Court of the District of Maryland, Case No. 1:07–cv–00718, Feb. 15, 2008.

Ozturk et al., "Kinetics of Release from Enteric–Coated Tablets," Pharmaceutical Research, 1988;5:550–565.

Ghebre–Sellassie et al., "Evaluation of acrylic–based modified–release film coatings," International Journal of Pharmaceutics, 1987;37:211–218.

Order and Memorandum Denying Colony's Motion for Partial Summary Judgment of Noninfringement of the '819 and '300 Patents in *Shire LLC* v. *Colony Pharmaceuticals, Inc.*, in the United States District Court for the District of Maryland, Case No. CCB–07–718, Jan. 2, 2008.

Plaintiff Shire LLC's Responses to Interrogatories Nos. 1–13 in *Shire LLC* v. *Colony Parmaceuticals, Inc.*, in the United States District Court for the District of Maryland, Case No. 1:07–cv–00718–CCB, Jun. 6, 2007.

Transcript of Richard A. Couch Deposition in *Shire LLC* v. *Colony Pharmaceuticals, Inc.* in the United States District Court for the District of Maryland, Case No. 1:07–cv–00718–CCB, Nov. 15, 2007.

Transcript of Beth A. Burnside Deposition in *Shire LLC* v. *Colony Pharmaceuticals*, in the United States District Court for the District of Maryland, Case No. 1:07–cv–00718–CCB, Nov. 9, 2007.

Transcript of Richard Rong–Kun Chang in *Shire LLC* v. *Colony Pharmaceuticals, Inc.* in the United States District Court for the District of Maryland, Case No. 1:07–cv–00718–CCB, Nov. 20, 2007.

Judgment and Order of Permanent Injunction in *Shire LLC* v. *Teva Pharmaceutical Industries Ltd.* in the United States District Court for the Eastern District of Pennsylvania, Civil Action No. 06–952–SD, Mar. 6, 2008.

Colony Pharmaceuticals, Inc.'s Responses to Plaintiff Shire LLC's Interrogatories (Nos. 1–7) in *Shire LLC* v. *Colony Pharmaceuticals, Inc.* in the United States District Court for the District of Maryland, Civil Action No. 1:07–cv–00718–CCB, May 29, 2007.

Judgment and Order of Permanaent Injunction in *Shire LLC* v. *Colony Pharmaceuticals, Inc.* in the United States District Court for the District of Maryland, Civil Action No. 1:07–cv–00718–CCB, Apr. 14, 2008.

Supplemental Expert Report of Vladimir P. Torchilin, Ph.D., D.Sc. Regarding the Invalidity of U.S. Patent No. 6,605,300 in *Shire LLC* v. *Colony Pharmaceuticals, Inc.* in the United States District Court for the District of Maryland, Civil Action No. 1:07–cv–00718–CCB and exhibits thereto, Feb. 15, 2008.

Plaintiff Shire LLC's Supplemental Responses to Interrogatory Nos. 1–5, 8, 9, & 12 in *Shire LLC* v. *Colony Pharmaceuticals, Inc.* in the United States District Court for the District of Maryland, Civil Action No. 1:07–cv–00718–CCB, Aug. 22, 2007.

Colony Pharmaceuticals, Inc.'s Amended Responses to Plaintiff Shire LLC's Interrogatories (Nos. 1–7) in *Shire LLC* v. *Colony Pharmaceuticals, Inc.* in the United States District Court for the District of Maryland, Civil Action No. 1:07–cv–00718–CCB, Jun. 5, 2007.

Colony Pharmaceuticals, Inc.'s Supplemental Responses to Plaintiff Shire LLC's Interrogatory Nos. 2–4 and 7 in *Shire LLC* v. *Colony Pharmaceuticals, Inc.* in the United States District Court for the District of Maryland, Civil Action No. 1:07–cv–00718–CCB, Sep. 5, 2007.

Actavis Elizabeth LLC's Supplemental Responses to Plaintiff Shire LLC's Interrogatory Nos. 5 and 6 in *Shire LLC* v. *Colony Pharmaceuticals, Inc.* in the United States District Court for the District of Maryland, Civil Action No. 1:07–cv–00718–CCB, Nov. 14, 2007.

Expert Report of Harry G. Brittain, Ph.D. FRSC in *Shire LLC* v. *Colony Pharmaceuticals, Inc.* in the United States District Court for the District of Maryland, Civil Action No. 1:07–cv–00718–CCB and exhibits thereto, Dec. 19, 2007.

Expert Report of Vladimir P. Torchilin, Ph.D., D.Sc. Regarding the Invalidity of U.S. patent No. 6,605,300 in *Shire LLC* v. *Colony Pharmaceuticals, Inc.* in the United States District Court for the District of Maryland, Civil Action No. 1:07–cv–00718–CCB and exhibits thereto, Dec. 20, 2007.

Corrected Expert Report of Vladimir P. Torchilin, Ph.D. D.Sc. Regarding the Invalidity of U.S. Patent No. 6,605,300 in *Shire LLC* v. *Colony Pharmaceuticals, Inc.* in the United States District Court for the District of Maryland, Civil Action No. 1:07–cv–00718–CCB, Dec. 21, 2007.
Memorandum of Law in Support of Defendants' Motion for Clarification or, in the Alternative for Reconsideration in *Shire LLC* v. *Colony Pharmaceuticals, Inc.* in the United States District Court for the District of Maryland, Civil Action No. 1:07–cv–00718–CCB, Jan. 16, 2008.
Memorandum of Law in Support of Defendants' Motion for Certification for Immediate Appeal Pursuant to 28 U.S.C. § 1292(b) in *Shire LLC* v. *Colony Pharmaceuticals, Inc.* in the United States District Court for the District of Maryland, Civil Action No. 1:07–cv–00718–CCB, Jan. 17, 2008.
Judgment and Order of Permanent Injunction in *Shire Laboratories, Inc.* v. *Andrx Pharmaceuticals, LLC* in the United States District Court for the Southern District of Florida, Miami Division, Case No. 07–22201–Civ–Cooke/Brown, Nov. 19, 2007.
Judgement and Order of Permanent Injunction in *Shire LLC* v. *Teva* Pharmaceutical in the United States District Court for the Eastern District of Pennsylvania, Civil Action No. 06–952–SD, Mar. 6, 2008.
Office Action issued Jul. 24, 2008 in U.S. Appl. No. 11/091, 011.
Neville et al., *Disintegration of Dextran Sulfate Tablet Products: Effect of Physicochemical Properties*, Drug Development and Industrial Pharmacy, New York, NY, vol. 18, No. 19, Jan. 1, 1992 (Jan. 1, 1992), pp. 2069–2079, XP009092848, ISSN: 0363–9045.
Patrick et al., *Pharmacology of Methylphenidate, Amphetamine Enantiomers and pemoline in Attention–Deficit Hyperactivity Disorder*, Human Psychopharmacology, vol. 12, pp. 527–546 (1997).
Chaumeil et al., *Enrobages gastro–resistants a l'acetophtalate de cellulose*, Annales Pharmaceutiques Francaises, 1973, No. 5, pp. 375–384.
U.S. Appl. No. 11/091,011, filed Apr. 7, 2009 Non–Final Office Action.
Office Action dated Dec. 6, 2007 in U.S. Appl. No. 11/091, 011.
Judgment and Order of Permanent in Shire Laboratories, Inc. and *Shire, LLC* v. *Andrx Pharmaceuticals, LLC, et al.*, In the United States District Court for the Southern District of Florida, Miami Division, Case No. 07–22201–CIV–Cooke/Brown, Nov. 19, 2007.
Answer and Counterclaims in *Shire Laboratories, Inc. and Shire, LLC* v. *Andrx Pharmaceuticals, LLC, et al.*, in the United States District Court for the Southern District of Florida, Case No. 07–22201–CIV–Cooke/Brown, Aug. 31, 2007.
Plaintiffs Shire Laboratories, Inc.'s and Shire LLC's Reply to Defendant Andrx Pharmaceuticals, LLC's Counterclaims in *Shire Laboratories, Inc. and Shire, LLC* v.*Andrx Pharmaceuticals, LLC, et al.*, in the United States District Court for the Southern District of Florida, Miami Division, Case No. 07–22201–CIV–Cooke/Brown, Sep. 24, 2007.
Second Amended Complaint for Patent Infringement and Declaratory Relief in *Shire Laboratories, Inc. and Shire, LLC* v. *Andrx Pharmaceuticals, LLC, et al.*, in the United States District Court for the Southern District of Florida, Miami Division, Case No. 07–22201–CIV–Cooke/Brown, Nov. 15, 2007.
Wigal, et al., Evaluation of Infividual Subjects in the Analog Clasroom Setting; II. Effects of Dose of Amphetamine (Adderall), Psychopharmacology Bulletin, vol. 34, No. 4, pp. 833–838, 1998.
Office Action dated Jun. 22, 2007 in Japanese patent Application No. 2000–576830.
Office Action dated Jun. 22, 2007 in U.S. Appl. No. 11/091, 011.
Amendment dated Sep. 24, 2007 in U.S. Appl. No. 11/091, 011.

* cited by examiner

ORAL PULSED DOSE DRUG DELIVERY SYSTEM

Matter enclosed in heavy brackets [ ] appears in the original patent but forms no part of this reissue specification; matter printed in italics indicates the additions made by reissue.

This application is a 371 of PCT/US99/24554 filed Oct. 20, 1999, which is continuation-in-part of application Ser. No. 09/176,542, filed Oct. 21, 1998, now U.S. Pat. No. 6,322,819 the contents of which are incorporated herein by reference.

This invention pertains to a multiple dosage form delivery system comprising one or more amphetamine salts for administering the amphetamine salts to a recipient.

BACKGROUND OF THE INVENTION

Traditionally, drug delivery systems have focused on constant/sustained drug output with the objective of minimizing peaks and valleys of drug concentrations in the body to optimize drug efficacy and to reduce adverse effects. A reduced dosing frequency and improved patient compliance can also be expected for the controlled/sustained release drug delivery systems, compared to immediate release preparations. However, for certain drugs, sustained release delivery is not suitable and is affected by the following factors:

First pass metabolism: Some drugs, such as β blockers, β-estradiol, and salicylamide, undergo extensive first pass metabolism and require fast drug input to saturate metabolizing enzymes in order to minimize presystemic metabolism. Thus, a constant/sustained oral method of delivery would result in reduced oral bioavailability.

Biological tolerance: Continuous release drug plasma profiles are often accompanied by a decline in the pharmacotherapeutic effect of the drug, e.g., biological tolerance of transdermal nitroglycerin.

Chronopharmacology and circadian rhythms: Circadian rhythms in certain physiological functions are well established. It has been recognized that many symptoms and onset of disease occur during specific time periods of the 24 hour day, e.g., asthma and angina pectoris attacks are most frequently in the morning hours (1,2).

Local therapeutic need: For the treatment of local disorders such as inflammatory bowel disease, the delivery of compounds to the site of inflammation with no loss due to absorption in the small intestine is highly desirable to achieve the therapeutic effect and to minimize side effects.

Gastric irritation or drug instability in gastric fluid: For compounds with gastric irritation or chemical instability in gastric fluid, the use of a sustained release preparation may exacerbate gastric irritation and chemical instability in gastric fluid.

Drug absorption differences in various gastrointestinal segments: In general, drug absorption is moderately slow in the stomach, rapid in the small intestine, and sharply declining in the large intestine. Compensation for changing absorption characteristics in the gastrointestinal tract may be important for some drugs. For example, it is rational for a delivery system to pump out the drug much faster when the system reaches the distal segment of the intestine, to avoid the entombment of the drug in the feces.

Pulsed dose delivery systems, prepared as either single unit or multiple unit formulations, and which are capable of releasing the drug after a predetermined time, have been studied to address the aforementioned problematic areas for sustained release preparations. These same factors are also problematic in pulsed dose formulations development. For example, gastrointestinal transit times vary not only from patient to patient but also within patients as a result of food intake, stress, and illness; thus a single-unit pulsed-release system may give higher variability compared to a multiple unit system. Additionally, drug layering or core making for multiple unit systems is a time-consuming and hard-to-optimize process. Particularly challenging for formulation scientists has been overcoming two conflicting hurdles for pulsatile formulation development, i.e., lag time and rapid release.

Various enteric materials, e.g., cellulose acetate phtalate, hydroxypropyl methylcellulose phtalate, polyvinyl acetate phthalate, and the EUDRAGIT® acrylic polymers, have been used as gastroresistant, enterosoluble coatings for single drug pulse release in the intestine (3). The enteric materials, which are soluble at higher pH values, are frequently used for colon-specific delivery systems. Due to their pH-dependent attributes and the uncertainty of gastric retention time, in-vivo performance as well as inter- and intra-subject variability are major issues for using enteric, coated systems as a time-controlled release of drugs.

A retarding swellable hydrophilic coating has been used for oral delayed release systems (4,5). It was demonstrated that lag time was linearly correlated with coating weight gain and drug release was pH independent.

Hydroxypropyl methylcellulose barriers with erodible and/or gellable characteristics formed using press coating technology for tablet dosage forms have been described to achieve time-programmed release of drugs (6). Barrier formulation variables, such as grade of hydroxypropyl methylcellulose, water-soluble and water-insoluble excipients, significantly altered the lag time and the release rate from the center cores.

Special grades of hydroxypropyl methylcellulose, e.g., METHOLOSE® 60SH, 90SH (Shin-Etsu Ltd., Japan), and METHOCEL® F4M (Dow Chemical Company, USA), as a hydrophilic matrix material have been used to achieve bimodal drug release for several drugs, i.e., aspirin, ibuprofen, and adinazolam (7). Bimodal release is characterized by a rapid initial release, followed by a period of constant release, and finalized by a second rapid drug release.

Tablets or capsules coated with a hydrophobic wax-surfactant layer, made from an aqueous dispersion of carnauba wax, beeswax, polyoxyethylene sorbitan monooleate, and hydroxypropyl methylcellulose have been used for rapid drug release after a predetermined lag time. However, even though a two-hour lag time was achieved for the model drug theophylline at a higher coating level (60%), three hours were required for a complete release of theophylline after the lag time. (8)

A sustained-release drug delivery system is described in U.S. Pat. No. 4,871,549. When this system is placed into dissolution medium or the gastrointestinal tract, water influx and the volume expansion of the swelling agent cause the explosion of the water permeable membrane. The drug thus releases after a predetermined time period. The OROS® push-pull system (Alza Company) has been developed for pulsatile delivery of water-soluble and water-insoluble drugs (9,10), e.g. the OROS-CT® system and is based on the swelling properties of an osmotic core compartment which provides a pH-independent, time-controlled drug release.

The PULSINCAP® dosage form releases its drug content at either a predetermined time or at a specific site (e.g., colon) in the gastrointestinal tract (11). The drug formulation is contained within a water-insoluble capsule body and is sealed with a hydrogel plug. Upon oral administration, the capsule cap dissolves in the gastric juice and the hydrogel plug swells. At a controlled and predetermined time point, the swollen plug is ejected from the PULSINCAP® dosage form and the encapsulated drug is released. A pulsatile capsule system containing captopril with release after a nominal 5-hr period was found to perform reproducibly in dissolution and gamma scintigraphy studies. However, in the majority of subjects, no measurable amounts of the drug were observed in the blood, possibly due to instability of the drug in the distal intestine. (12)

ADDERALL® comprises a mixture of four amphetamine salts, dextroamphetamine sulfate, dextroamphetamine saccharate, amphetamine asparate monohydrate and amphetamine sulfate, which in combination, are indicated for treatment of Attention Deficity Hyperactivity Disorder in children from 3–10 years of age. One disadvantage of current treatment is that a tablet form is commonly used which many young children have difficulty in swallowing. Another disadvantage of current treatment is that two separate dose are administered, one in the morning and one approximately 4–6 hours later, commonly away from home under other than parental supervision. This current form of treatment, therefore, requires a second treatment which is time-consuming, inconvenient and may be problematic for those children having difficulty in swallowing table formulations.

SUMMARY OF THE INVENTION

Accordingly, in view of a need for successfully administering a multiple unit pulsed dose of amphetamine salts and mixtures thereof, the present invention provides an oral multiple unit pulsed dose delivery system for amphetamine salts and mixtures thereof. FIG. 1 illustrates the desired target plasma level profile of the pharmaceutical active contained within the delivery system.

In accordance with a preferred embodiment of the present invention, there is provided a pharmaceutical composition for delivering one or more pharmaceutically active amphetamine salts that includes:

(a) one or more pharmaceutically active amphetamine salts that are covered with an immediate release coating, and (b) one or more pharmaceutically active amphetamine salts that are covered with an enteric release coating wherein (1) the enteric release coating has a defined minimum thickness and/or (2) there is a protective layer between the at least one pharmaceutically active amphetamine salt and the enteric release coating and/or (3) there is a protective layer over the enteric release coating.

In one embodiment, the immediate release and enteric release portions of the composition are present on the same core.

In another embodiment, the immediate release and enteric release components are present on different cores.

It is also contemplated that the composition may include a combination of the hereinabove referred to cores (one or more cores that include both components on the same core and one or more cores that include only one of the two components on the core).

The present invention provides a composition in which there is immediate release of drug and enteric release of drug wherein the enteric release is a pulsed release and wherein the drug includes one or more amphetamine salts and mixtures thereof.

The immediate release component releases the pharmaceutical agent in a pulsed dose upon oral administration of the delivery system.

The enteric release coating layer retards or delays the release of the pharmaceutical active or drug for a specified time period ("lag time") until a predetermined time, at which time the release of the drug is rapid and complete, i.e., the entire dose is released within about 30–60 minutes under predetermined environmental conditions, i.e. a particular location within the gastrointestinal tract.

The delay or lag time will take into consideration factors such as transit times, food effects, inflammatory bowel disease, use of antacids or other medicaments which alter the pH of the GI tract.

In a preferred embodiment, the lag time period is only time-dependent, i.e., pH independent. The lag time is preferably within 4 to 6 hours after oral administration of the delivery system.

In one aspect, the present invention is directed to a composition that provides for enteric release of at least one pharmaceutically active amphetamine salt, including at least one pharmaceutically active amphetamine salt that is coated with an enteric coating wherein (1) the enteric release coating has a defined minimum thickness and/or (2) there is a protective layer between the at least one pharmaceutically active amphetamine salt and the enteric release coating and/or (3) there is a protective layer over the enteric release coating.

In attempting to provide for enteric release of an amphetamine salt, applicants found that use of an enteric release coating as generally practiced in the art did not provide effective enteric release.

Typical enteric coating levels did not meet the above requirements for the desired dosage profile of amphetamine salts. Using the typical amount of enteric coating (10–20μ) resulted in undesired premature leakage of the drug from the delivery system into the upper gastrointestinal tract and thus no drug delivery at the desired location in the gastrointestinal tract after the appropriate lag time. Thus this coating did not meet the requirements for the drug release profile to provide full beneficial therapeutic activity at the desired time.

Surprisingly, applicants found that using a thicker application of enteric coating on the formulation allowed for the second pulsed dose to be released only and completely at the appropriate time in the desired predetermined area of the gastrointestinal tract, i.e., in the intestine.

This was surprising because an increase in thickness of about 5–10μ of enteric coatings above a minimum thickness of about 10–20μ typically does not have a significant effect on release of drug from within such coatings. Enteric coatings typically are pH dependent and will only dissolve/disperse when exposed to the appropriate environment. Typically, application of a thicker coating (greater than 20μ) will only marginally increase the time for complete release at the appropriate environmental condition i.e., for a brief period of time (20 minutes). Using the typical coating, applicants could not achieve the desired result—rather, the coating leaked before the predetermined time in an inappropriate environment resulting in significant loss of the therapeutic agent.

Accordingly, in one aspect, the pulsed enteric release of the amphetamine salts is accomplished by employing a certain minimum thickness of the enteric coating.

In one embodiment of the invention, the pulsed dose delivery comprises a composition which comprises one or more pharmaceutically active amphetamine salts; an enteric coating over the one or more pharmaceutically active amphetamine salts, wherein the thickness of the enteric coating layer is at least 25μ; a further layer of one or more pharmaceutically active amphetamine salts over the enteric coating layer; and an immediate release layer coating. The thicker enteric coating surprisingly provides the required delayed immediate release of the pharmaceutically active amphetamine salt at the desired time in the desired area of the gastrointestinal tract. FIG. 2 illustrates a model of this delivery system.

In this aspect, the one or more pharmaceutically active amphetamine salts can be provided within or as a part of a core seed around which the enteric coating is applied. Alternatively, a core seed can be coated with one or more layers of one or more pharmaceutically active amphetamine salts.

It has further been discovered that a delayed immediate release drug delivery can also be accomplished by coating the drug first with a protective layer prior to applying the enteric coating.

Thus, in another embodiment, the pulsed enteric release is accomplished by employing a protective layer between the drug and the enteric coating. When using a protective coating, the enteric coating may be of an increased thickness or may be of lower thickness.

Thus, in another aspect, the object of the invention is met by providing a composition comprising one or more pharmaceutically active amphetamine salts; a protective layer coating over the one or more pharmaceutically active amphetamine salt layer(s), and an enteric coating layer over the protective coating layer; a further pharmaceutically active amphetamine salt layer and an immediate release layer coating. In a preferred embodiment of this aspect, the thickness of the enteric coating is at least 25μ, and the protective layer comprises an immediate release coating.

With respect to this embodiment of the invention, the one or more pharmaceutically active amphetamine salts can be provided within or as a part of a core seed, during the core seed manufacturing process, around which the protective coating is applied. Alternatively, a core seed can be coated with one or more layers of one or more pharmaceutically active amphetamine salts.

In another embodiment, the pulsed enteric release is accomplished by employing a protective layer over the enteric coating.

Accordingly, in this embodiment of the present invention, there is provided a pulsed dose release drug delivery system comprising one or more pharmaceutically active amphetamine salts; an enteric coating layer over the pharmaceutically active amphetamine salt layer(s); and a protective layer over the enteric coating; a second pharmaceutically active amphetamine salt layer; and an immediate release layer coating.

In one aspect of this embodiment, the protective layer is comprised of one or more components, which includes an immediate release layer and a modifying layer. The modifying layer is preferably comprised of a semi water-permeable polymer. Applicants have surprisingly found that a semi-permeable polymer coating used in combination with an immediate release layer coating provided a delayed pulsed release drug delivery profile when layered over the enteric coating.

Thus, in this embodiment, the protective layer comprises a semi-permeable polymer and an immediate release coating layer. In a preferred embodiment, the modifying layer comprises a first layer of a semi-permeable polymer which is adjacent to the enteric coating layer and a second coating layer over the semi-permeable polymer coating layer comprising an immediate release polymer coating layer.

In one aspect of this embodiment, a semi-permeable polymer, which may comprise a low water-permeable pH-insensitive polymer, is layered onto the outer surface of the enteric layer, in order to obtain prolonged delayed release time. This semi-permeable polymer coating controls the erosion of the pH-sensitive enteric polymer in an alkaline pH environment in which a pH-sensitive polymer will dissolve rapidly. Another pH-sensitive layer may be applied onto the surface of a low water-permeability layer to further delay the release time.

In a still further aspect of the invention, in addition to a protective layer, the composition comprises an acid which is incorporated into the pharmaceutical active layer or coated onto the surface of the active layer to reduce the pH value of the environment around the enteric polymer layer. The acid layer may also be applied on the outer layer of the pH-sensitive enteric polymer layer, followed by a layer of low water-permeability polymer. The release of the active thus may be delayed and the dissolution rate may be increased in an alkaline environment.

In a further embodiment, the protective coating may be used both over the drug and over the enteric coating.

With respect of this embodiment of the invention, the one or more pharmaceutically active amphetamine salts can be provided within or as a part of a core seed, during the core seed manufacturing process, around which the enteric coating is applied. Alternatively, a core seed can be coated with one or more layers of one or more pharmaceutically active amphetamine salts.

The drug delivery system of the present invention as described herein preferably comprises one or a number of beads or beadlets in a dosage form, either capsule, tablet, sachet or other method of orally administering the beads.

DETAILED DESCRIPTION OF THE INVENTION

Figure 1:
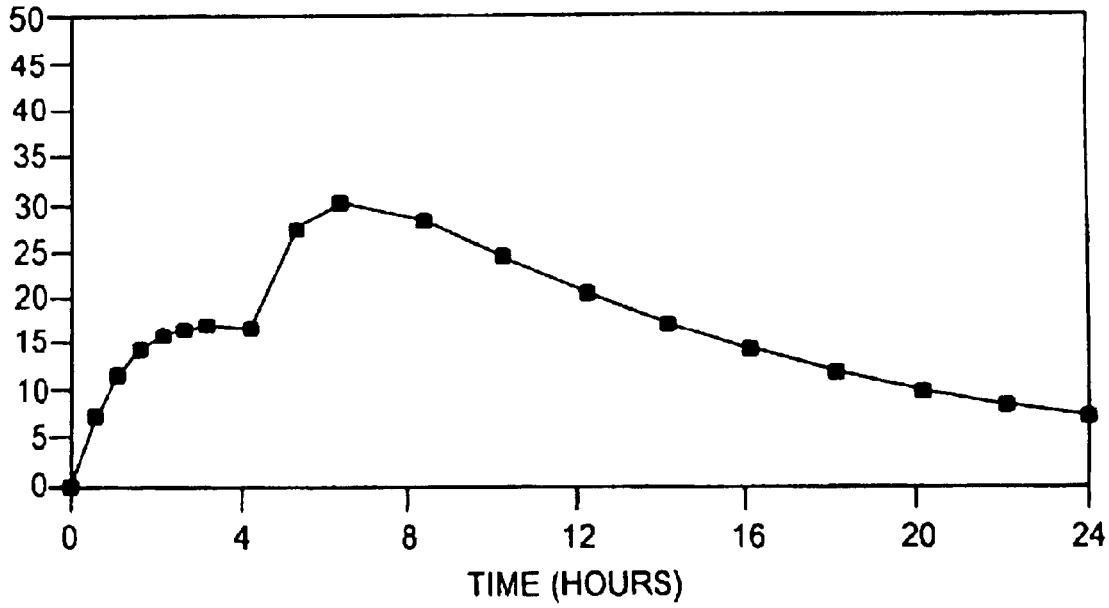
FIG. 1 illustrates a multiple pulse drug delivery system target plasma profile of the drug delivery system of the present invention. The profile reflects an immediate-release component followed by a delayed-release component.
Figure 2A:
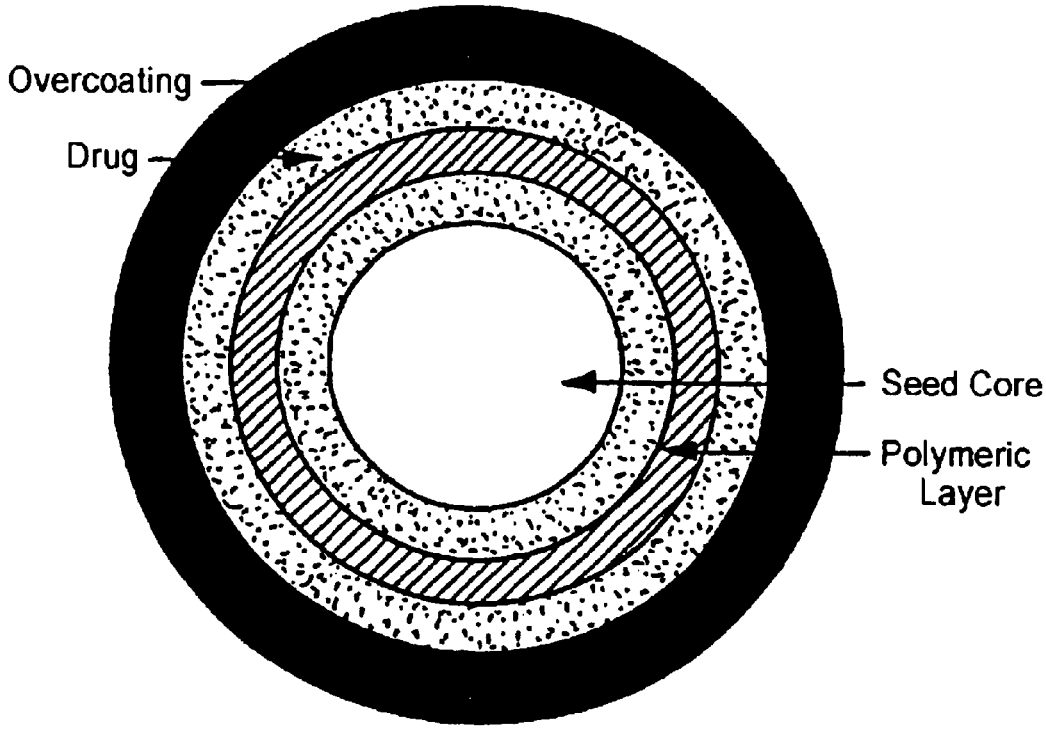
FIG. 2a graphically illustrates a pulsed dose delivery system.
Figure 2B:
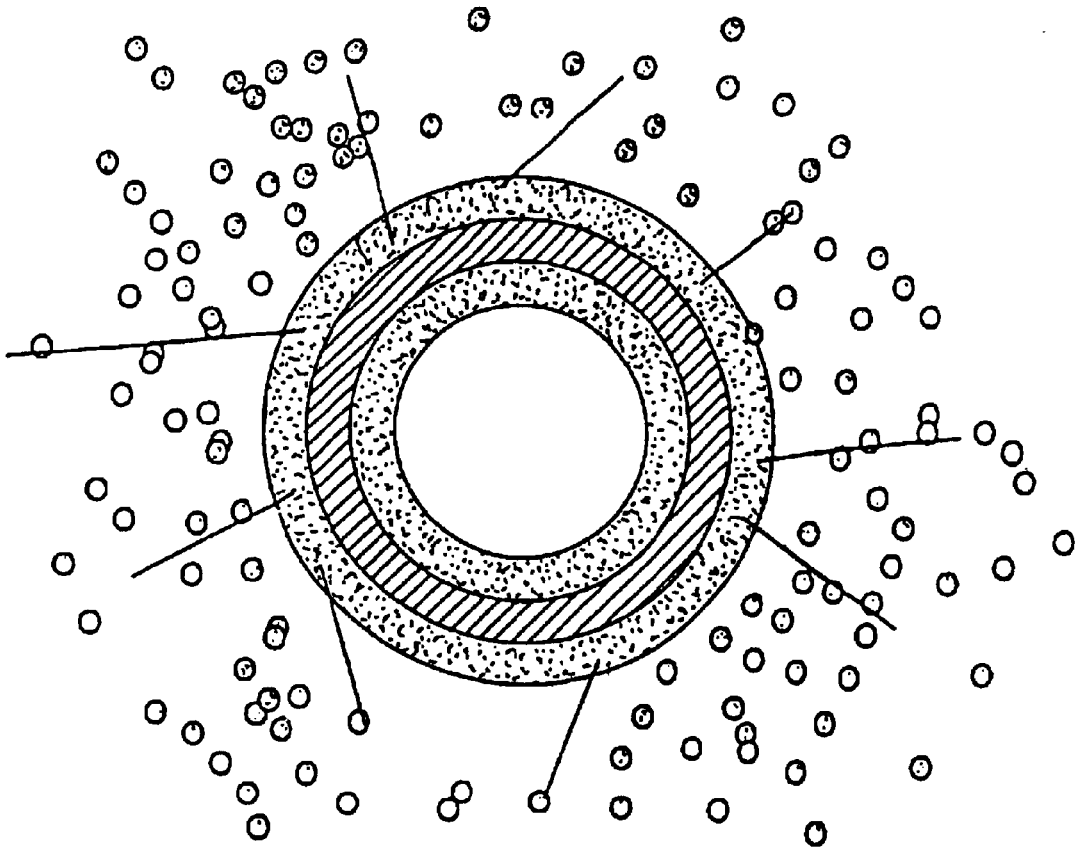
FIGS. 2b and c graphically illustrate the drug release mechanism from the proposed delivery system.
Figure 2C:
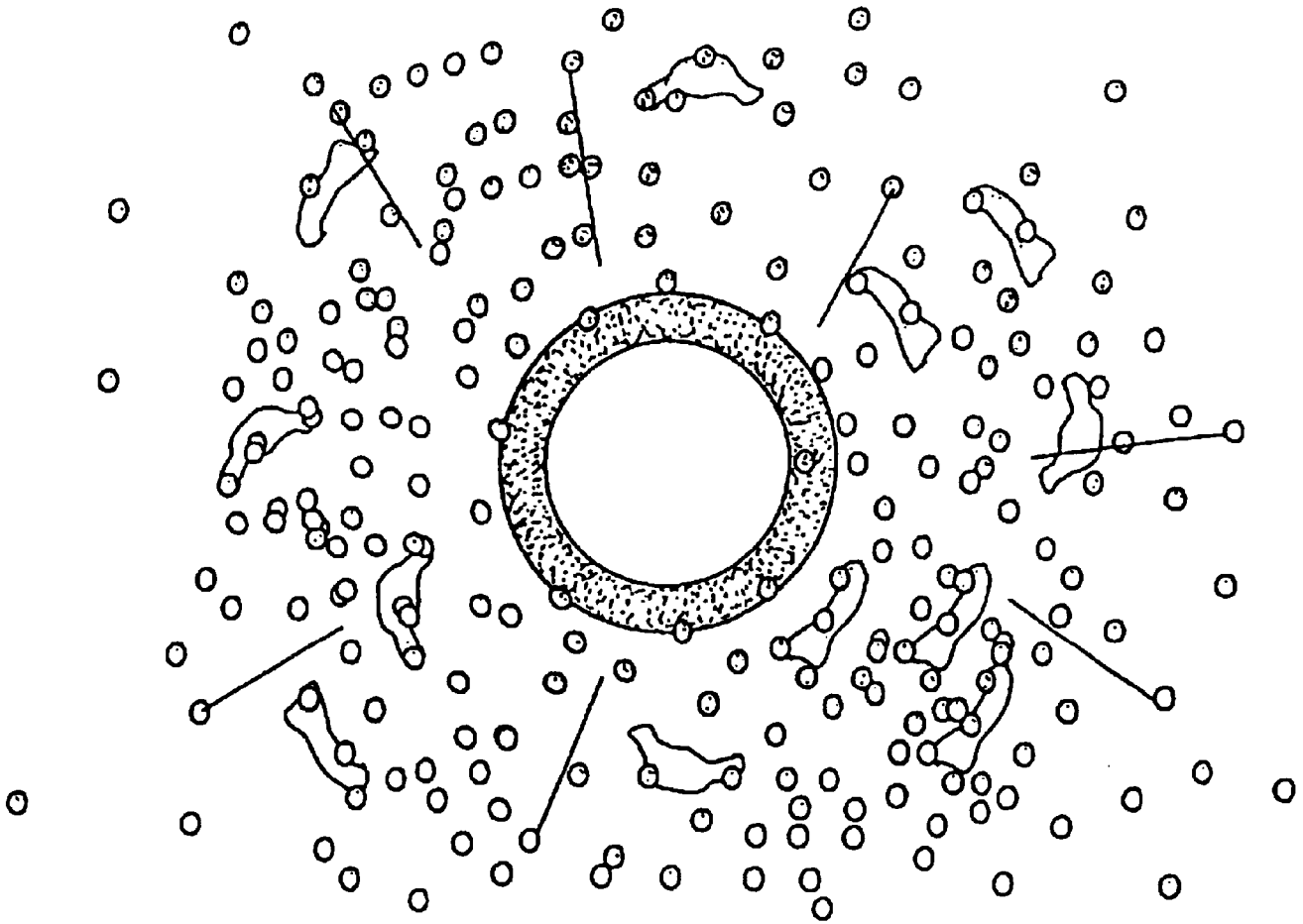

The present invention comprises a core or starting seed, either prepared or commercially available product. The cores or starting seeds can be sugar spheres; spheres made from microcrystalline cellulose and any suitable drug crystals.

The materials that can be employed in making drug-containing pellets are any of those commonly used in pharmaceutics and should be selected on the basis of compatibility with the active drug and the physicochemical properties of the pellets. The additives except active drugs are chosen below as examples.

Binders such as cellulose derivatives such as methylcellulose, hydroxyethyl cellulose, hydroxypropyl cellulose, hydroxypropyl methylcellulose, polyvinylpyrrolidone, polyvinylpyrrolidone/vinyl acetate copolymer and the like.

Disintegration agents such as corn starch, pregelatinized starch, cross-linked carboxymethylcellulose (AC-DI-SOL®), sodium starch glycolate (EXPLOTAB®), cross-linked polyvinylpyrrolidone (PLASDONE XL®), and any disintegration agents used in tablet preparations.

Filling agents such as lactose, calcium carbonate, calcium phosphate, calcium sulfate, microcrystalline cellulose, dextran, starches, sucrose, xylitol, lactitol, mannitol, sorbitol, sodium chloride, polyethylene glycol, and the like.

Surfactants such as sodium lauryl sulfate, sorbitan monooleate, polyoxyethylene sorbitan monooleate, bile salts, glyceryl monostearate, PLURONIC® line (BASF), and the like.

Solubilizers such as citric acid, succinic acid, fumaric acid, malic acid, tartaric acid, maleic acid, glutaric acid sodium bicarbonate and sodium carbonate and the like.

Stabilizers such as any antioxidation agents, buffers, acids, and the like, can also be utilized.

Methods of manufacturing the core include a. Extrusion-Spheronization—Drug(s) and other additives are granulated by addition of a binder solution. The wet mass is passed through an extruder equipped with a certain size screen. The extrudates are spheronized in a marumerizer. The resulting pellets are dried and sieved for further applications.

b. High-Shear Granulation—Drug(s) and other additives are dry-mixed and then the mixture is wetted by addition of a binder solution in a high shear-granulator/mixer. The granules are kneaded after wetting by the combined actions of mixing and milling. The resulting granules or pellets are dried and sieved for further applications.

c. Solution or Suspension Layering—A drug solution or dispersion with or without a binder is sprayed onto starting seeds with a certain particle size in a fluid bed processor or other suitable equipment. The drug thus is coated on the surface of the starting seeds. The drug-loaded pellets are dried for further applications.

For purposes of the present invention, the core particles have a diameter in the range of about 50–1500 microns; preferably 100–800 microns.

These particles can then be coated in a fluidized bed apparatus with an alternating sequence of coating layers.

The core may be coated directly with a layer or layers of at least one pharmaceutically active amphetamine salts and/or the pharmaceutically active amphetamine salt may be incorporated into the core material. Pharmaceutical active amphetamine salts contemplated to be within the scope of the present invention include amphetamine base, all chemical and chiral derivatives and salts thereof; methylphenidate, all chemical and chiral derivatives and salts thereof; phenylpropanolamine and its salts; and all other compounds indicated for the treatment of attention deficit hyperactivity disorder (ADHD).

A protective layer may be added on top of the pharmaceutical active containing layer and also may be provided between active layers. A separation or protective layer may be added onto the surface of the active-loaded core, and then the enteric layer is coated thereupon. Another active layer may also be added to the enteric layer to deliver an initial dose.

A protective coating layer may be applied immediately outside the core, either a drug-containing core or a drug-layered core, by conventional coating techniques such as pan coating or fluid bed coating using solutions of polymers in water or suitable organic solvents or by using aqueous polymer dispersions. Suitable materials for the protective layer include cellulose derivatives such as hydroxyethyl cellulose, hydroxypropyl cellulose, hydroxypropyl methylcellulose, polyvinylpyrrolidone, polyvinylpyrrolidone/vinyl acetate copolymer, ethyl cellulose aqueous dispersions (AQUACOAT®, SURELEASE®), EUDRAGIT® RL 30D, OPADRY® and the like. The suggested coating levels are from 1 to 6%, preferably 2–4% (w/w).

The enteric coating layer is applied onto the cores with or without seal coating by conventional coating techniques, such as pan coating or fluid bed coating using solutions of polymers in water or suitable organic solvents or by using aqueous polymer dispersions. All commercially available pH-sensitive polymers are included. The pharmaceutical active is not released in the acidic stomach environment of approximately below pH 4.5, but not limited to this value. The pharmaceutical active should become available when the pH-sensitive layer dissolves at the greater pH, after a certain delayed time; or after the unit passes through the stomach. The preferred delay time is in the range of two to six hours.

Enteric polymers include cellulose acetate phthalate, Cellulose acetate trimellitate, hydroxypropyl methylcellulose phtalate, polyvinyl acetate phtalate, carboxymethylethylcellulose, co-polymerized methacrylic acid/methacrylic acid methyl esters such as, for instance, materials known under the trade name EUDRAGIT® L12.5, L100, or EUDRAGIT® S12.5, S100 or similar compounds used to obtain enteric coatings. Aqueous collodial polymer dispersions or re-dispersions can be also applied, e.g. EUDRAGIT® L 30D-55, EUDRAGIT® L100-55, EUDRAGIT® S100, EUDRAGIT® preparation 4110D (Rohm Pharma); AQUATERIC®, AQUACOAT® CPD 30 (FMC); KOLLICOAT MAE® 30D and 30DP (BASF); EASTACRYL® 30D (Eastman Chemical).

The enteric polymers used in this invention can be modified by mixing with other known coating products that are not pH sensitive. Examples of such coating pro ducts include the neutral methacrylic acid esters with a small portion of trimethylammonioethyl methacrylate chloride, sold currently under the trade names EUDRAGIT® RS and EUDRAGIT® RL; a neutral ester dispersion without any functional groups, sold under the trade names EUDRAGIT® NE30D; and other pH independent coating products.

The modifying component of the protective layer used over the enteric coating can include a water penetration barrier layer (semipermeable polymer) which can be successively coated after the enteric coating to reduce the water penetration rate through the enteric coating layer and thus increase the lag time of the drug release. Sustained-release coatings commonly known to one skilled in the art can be used for this purpose by conventional coating techniques such as pan coating or fluid bed coating using solutions of polymers in water or suitable organic solvents or by using aqueous polymer dispersions. For example, the following materials can be used, but not limited to: Cellulose acetate, Cellulose acetate butyrate, Cellulose acetate propionate, Ethyl cellulose, Fatty acids and their esters, Waxes, zein, and aqueous polymer dispersions such as EUDRAGIT® RS and SURELEASE®, cellulose acetate latex. The combination of above polymers and hydrophilic polymers such as Hydroxyethyl cellulose, Hydroxypropyl cellulose (KLUCEL®, Hercules Corp.), Hydroxypropyl methylcellulose (METHOCEL®, Dow Chemical Corp.), Polyvinylpyrrolidone can also be used.

An overcoating layer can further optionally be applied to the composition of the present invention. OPADRY®, OPADRY II® (Colorcon) and corresponding color and colorless grades from Colorcon can be used to protect the pellets from being tacky and provide colors to the product. The suggested levels of protective or color coating are from 1 to 6%, preferably 2–3% (w/w).

Many ingredients can be incorporated into the overcoating formula, for example to provide a quicker immediate release, such as plasticizers: acetyltriethyl citrate, triethyl citrate, acetyltributyl citrate; dibutylsebacate, triacetin, polyethylene glycols, propylene glycol and the others; lubricants: talc, colloidal silica dioxide, magnesium stearate, calcium stearate, titanium dioxide, magnesium silicate, and the like.

The composition, preferably in beadlet form, can be incorporated into hard gelatin capsules, either with additional excipients, or alone. Typical excipients to be added to a capsule formulation include, but are not limited to: filters such as microcrystalline cellulose, soy polysaccharides, calcium phosphate dihydrate, calcium sulfate, lactose, sucrose, sorbitol, or any other inert filler. In addition, there can be flow aids such as fumed silicon dioxide, silica gel, magnesium stearate, calcium stearate or any other material imparting flow to powders. A lubricant can further be added if necessary by using polyethylene glycol, leucine, glyceryl behenate, magnesium stearate or calcium stearate.

The composition may also be incorporated into a tablet, in particular by incorporation into a tablet matrix, which rapidly disperses the particles after ingestion. In order to incorporate these particles into such a tablet, a filler/binder must be added to a table that can accept the particles, but will not allow their destruction during the tableting process. Materials that are suitable for this purpose include, but are not limited to, microcrystalline cellulose (AVICEL®), soy polysaccharide (EMCOSOY®), pre-gelatinized starches (STARCH® 1500, NATIONAL® 1551), and polyethylene glycols (CARBOWAX®). The materials should be present in the range of 5–75% (w/w), with a preferred range of 25–50% (w/w).

In addition, disintegrants are added in order to dispense the beads once the tablet is ingested. Suitable disintegrants include, but are not limited to: cross-linked sodium carboxymethyl cellulose (AC-DI-SOL®), sodium starch glycolate (EXPLOTAB®, PRIMOJEL®), and cross-linked polyvinylpolypyrrolidone (Plasone-XL). These materials should be present in the rate of 3–15% (w/w), with a preferred range of 5–10% (w/w).

Lubricants are also added to assure proper tableting, and these can include, but are not limited to: magnesium stearate, calcium stearate, stearic acid, polyethylene glycol, leucine, glyceryl behanate, and hydrogenated vegetable oil. These lubricants should be present in amounts from 0.1–10% (w/w), with a preferred range of 0.3–3.0% (w/w).

Tablets are formed, for example, as follows. The particles are introduced into a blender along with AVICEL®, disintegrants and lubricant, mixed for a set number of minutes to provide a homogeneous blend which is then put in the hopper of a tablet press with which tablets are compressed. The compression force used is adequate to form a tablet; however, not sufficient to fracture the beads or coatings.

It will be appreciated that the multiple dosage form of the present invention can deliver rapid and complete dosages of pharmaceutically active amphetamine salts to achieve the desired levels of the drug in a recipient over the course of about 8 hours with a single oral administration.

In so doing, the levels of drug in blood plasma of the pharmaceutically active amphetamine salts will reach a peak fairly rapidly after about 2 hours, and after about 4 hours a second pulse dose is released, wherein a second fairly rapid additive increase of plasma drug levels occurs which slowly decreases over the course of the next 12 hours.

The following examples are presented to illustrate and do not limit the invention.

EXAMPLES

Example 1

Immediate Release Formulation

The following formulation was used to layer the drug onto sugar spheres. Nonpareil seeds (30/35 mesh, Paulaur Corp., NJ), 6.8 kg were put into a FLM-15 fluid bed processor with a 9" Wurster column and fluidized at 60° C. The suspension of mixed amphetamine salts (MAS) with 1% HPMC E5 Premium (Dow Chemical) as a binder was sprayed onto the seed under suitable conditions. Almost no agglomeration and no fines were observed with a yield of at least 98%. The drug-loaded cores were used to test enteric coatings and sustained release coatings.

TABLE 1

| Ingredients | Amount (%) |
|---|---|
| Nonpareil seed | 88.00 |
| mixed amphetamine salts | 11.40 |
| METHOCEL ® E5 Premium | 0.60 |
| Water | * |

*removed during processing

Figure 3:
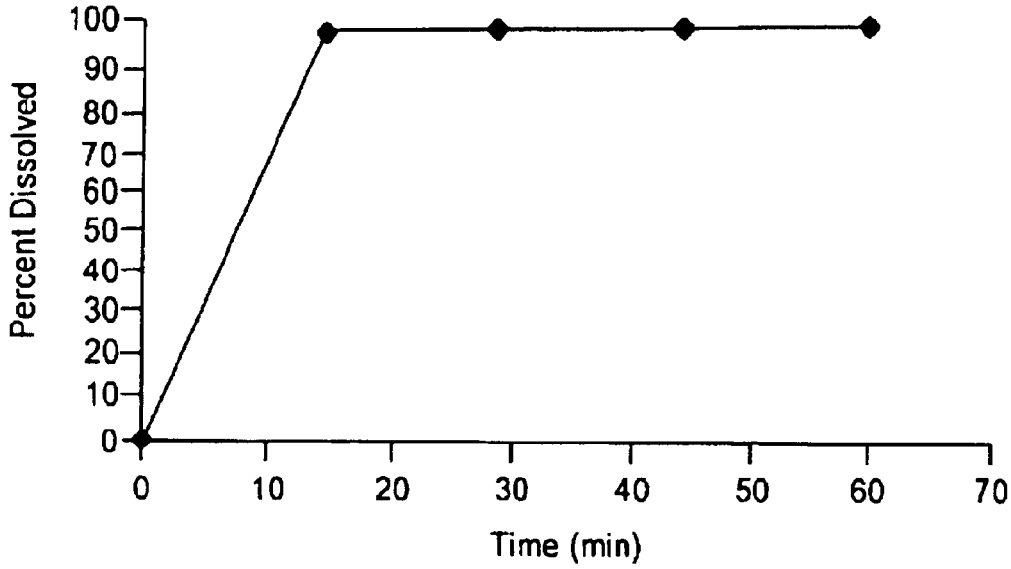
FIG. 3 is a plot of the present drug released versus time from the drug-loaded pellets described in Example 1 which exemplifies the immediate release component of the present invention.

The drug release profile of the drug-loaded pellets of this example is shown in FIG. 3.

Example 2

The following formulation was used to coat the mixed amphetamine salts loaded (MASL) pellets from Example 1 with the EUDRAGIT® L 30D-55 (Rohm Pharma, Germany) coating dispersion. 2 kg of MASL pellets were loaded into a fluid bed processor with a reduced Wurster column equipped with a precision coater [(MP 2/3, Niro Inc)] (*see Examples 3 and 4*). The coating dispersion was prepared by dispersing Triethyl citrate, Talc and EUDRAGIT® L 30D-55 into water and mixing for at least 30 minutes. Under suitable fluidization conditions, the coating dispersion was sprayed onto the fluidized MASL pellets. The spraying was continued until the targeted coating level was achieved [(20 μ)]. The coated pellets were dried at 30–35° C. for 5 minutes before stopping the process. The enteric coated [PPA] *MASL* pellets were tested at different pH buffers by a USP paddle method. The drug content was analyzed using HPLC. The results showed that the enteric coating delayed the drug release from the coated pellets until after exposure to pH 6 or higher. (Reference #AR98125-4)

TABLE 2

| Ingredients | Amount (%) |
|---|---|
| MASL pellets | [40.00]*70.00* |
| EUDRAGIT ® L 30D-55 | 24.88 |
| Triethyl citrate | 2.52 |
| Talc | 2.60 |
| Water | * |

*removed during processing

Figure 4:
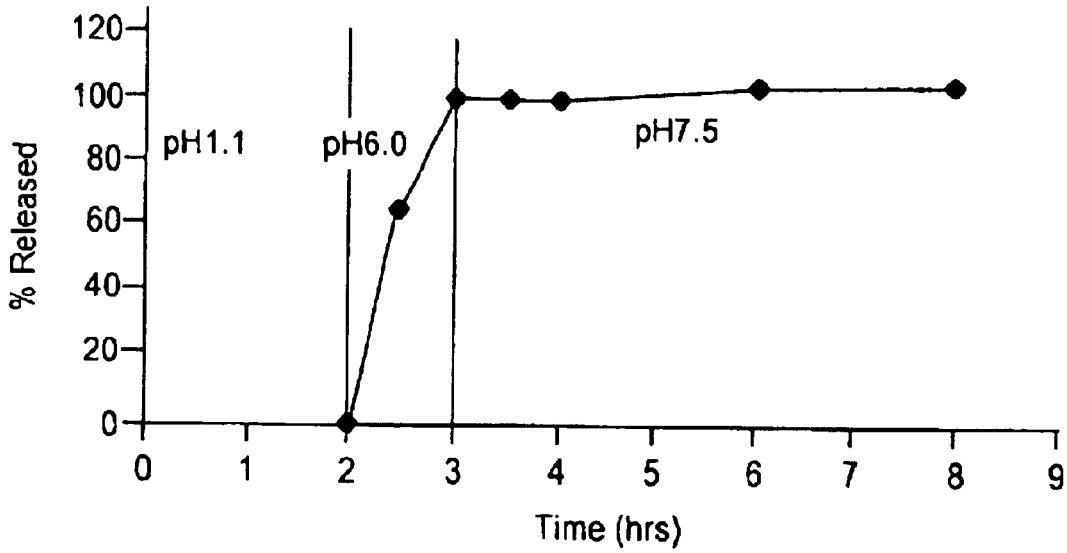
FIG. 4 is a plot of the percent drug released versus time from the coated pellets described in Example 2 which exemplifies [the immediate release component and] the delayed release components of the present invention.

The drug release profile of the coated pellets of this example is shown in FIG. 4.

Example 3

The following formulation was used to coat the MASL pellets from Example 1 with the EUDRAGIT® 4110D (Rohm Pharma, Germany) coating dispersion. MASL pellets (2 kg) were loaded in a fluid bed processor with a reduced Wurster column (GPGC-15, Glatt). The coating dispersion was prepared by dispersing Triethyl citrate, Talc and EUDRAGIT® 4110D into water and mixing for at least 30 minutes. Under suitable fluidization conditions, the coating dispersion was sprayed onto the fluidized MASL pellets. The spraying was continued until the targeted coating level was achieved. The coated pellets were dried at 30–35° C. for 5 minutes before stopping the process. The enteric coated MASL pellets were tested using a USP paddle method at different pH buffers. The drug content was analyzed using HPLC. The enteric coating delayed the drug release for several hours from the coated pellets until the pH value reached 6.8 or higher, as shown below in Table 3. (Reference #AR98125-3)

TABLE 3

| Ingredients | Amount (%) |
|---|---|
| MASL pellets | [70.00] |
| EUDRAGIT ® 4110D | [26.24] |
| Triethyl citrate | [0.76] |
| Talc | [3.00] |
| Water | * |

*removed during processing

Figure 5:
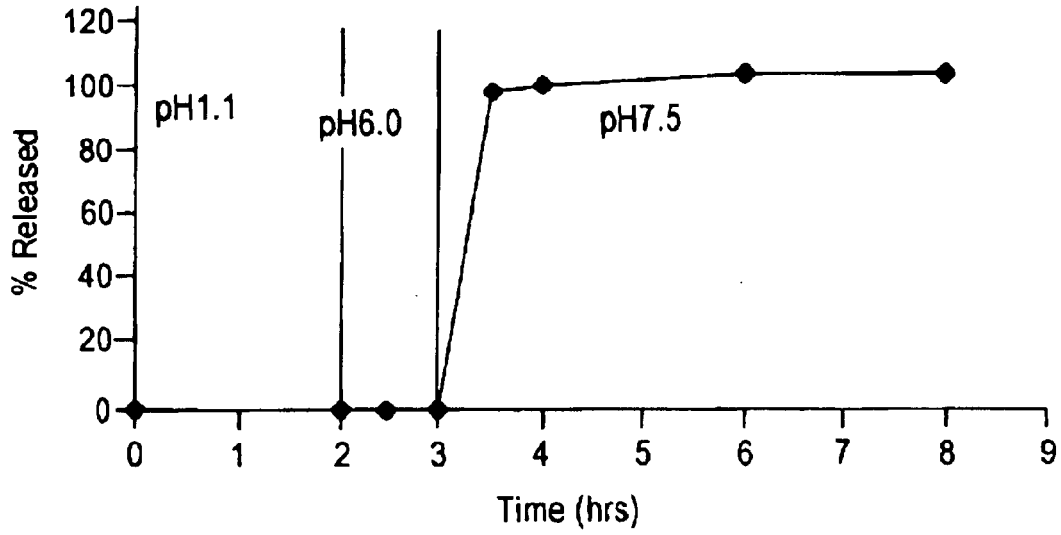
FIG. 5 is a plot of the percent drug released versus time from the coated pellets described in Example 3 which exemplifies [the immediate release component and] the delayed release components of the present invention.

The drug release profile of coated pellets of this example is shown in FIG. 5.

Example 4

The following formulation was selected to coat the enteric coated MASL pellets. Coated MASL pellets from Example 2 or coated MASL pellets from Example 3 (2 kg of either) were loaded into a fluid bed processor with a reduced Wurster column (GPGC-15, Glatt). The coating dispersion was prepared by mixing SURELEASE® (Colorcon) and water for at least 15 minutes prior to spraying. Under suitable fluidization conditions, the coating dispersion was sprayed onto the fluidizated pellets. The spraying was continued until the targeted coating level was achieved. The coated pellets were coated with a thin layer of OPADRY® white (Colorcon) (2%) to prevent the tackiness of the coated pellets during storage. The coated pellets were then dried at 35–40° C. for 10 minutes before discharging from the bed. The drug dissolution from both coated pellets was performed using a USP paddle method at different pH buffers. The drug content was analyzed using HPLC. The 8% SURELEASE® coating slightly sustained the drug release from EUDRAGIT® L 30D-55 coated pellets at pH 7.5 buffer, while the SURELEASE® coating delayed the drug release up to 2 hours after the buffer switched from pH 1 to pH 7.5. (Reference ##AR98125-1)

TABLE 4

| Ingredients | Amount, (%) |
|---|---|
| Enteric coated MASL pellets | 90.00 |
| SURELEASE ® | 8.00 |
| OPADRY ® white | 2.00 |
| Water | * |

*removed during processing

Figure 6:
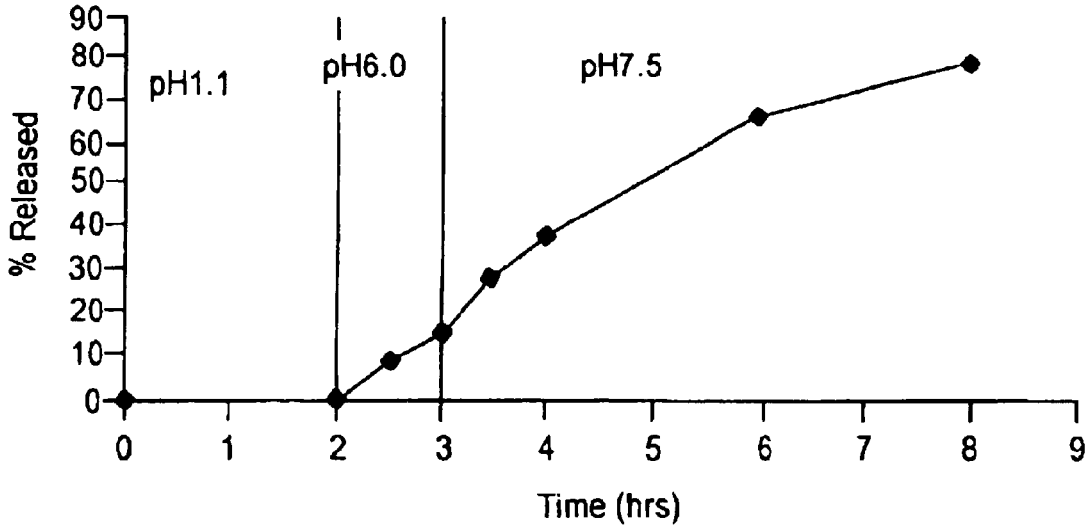
FIG. 6 illustrates the drug release profile of coated pellets described in Example 4 which exemplifies [the immediate release component and] the delayed release components of the present invention.

The drug release profile of the coated pellets from this example is shown in FIG. 6.

Example 5

Figure 7:
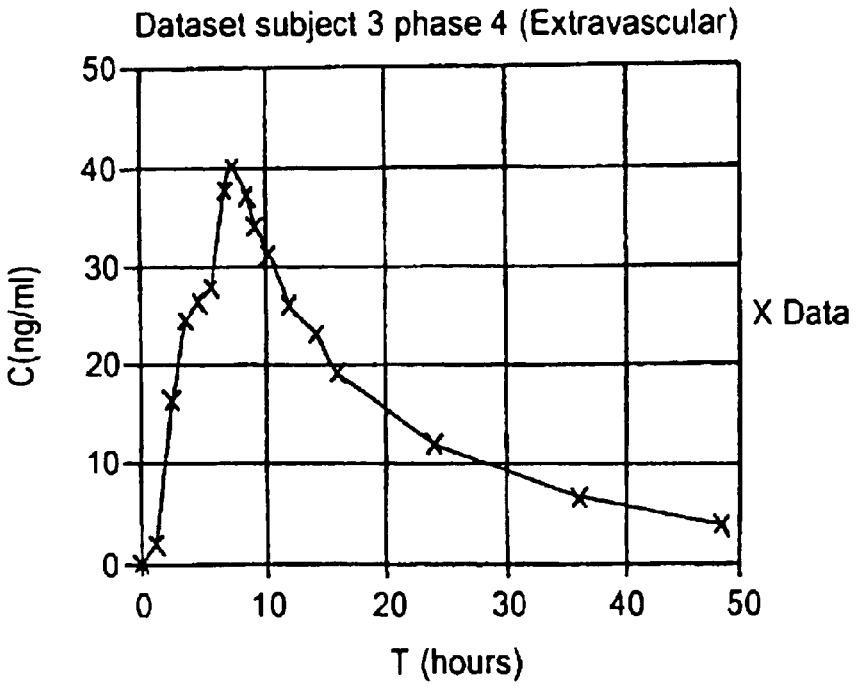
FIG. 7 is a plot of a profile of plasma amphetamine concentration after administration of a composite capsule containing the immediate release pellets and delayed release pellets from Examples 1 and 2, respectively.
Figure 8:
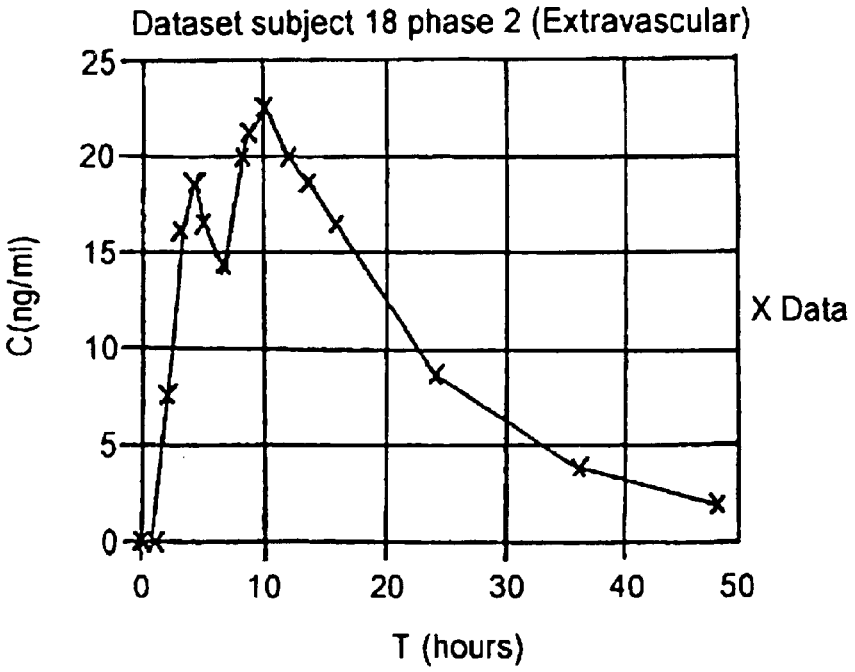
FIG. 8 is a plot of a profile of plasma amphetamine concentration after administration of a composite capsule containing the immediate release pellets and delayed release pellets from Examples 1 and 3, respectively.

A pulsatile delivery system can be achieved by combining the immediate release pellets (Example 1) with delayed release pellets (Example 2 or Example 3). The immediate-release pellets equivalent to half the dose and the delayed-release pellets equivalent to half the dose are filled into a hard gelatin capsule to produce the oral pulsed dose delivery system. The delayed-release portion releases the amphetamine salts rapidly and completely, after a specified lag time. The capsule products containing immediate-release pellets and delayed-release pellets (Example 1 plus Example 2 and Example 1 plus Example 3) were tested in a crossover human study. FIGS. 7 and 8 show the typical profiles of plasma amphetamine concentration after administration of a composite capsule containing the immediate-release pellets and delayed-release pellets from Examples 1 and 2 (10 mg dose each pellet type) and a capsule containing the pellets from immediate-release pellets and delayed-release pellets from Examples 1 and 3 (10 mg dose each pellet type), respectively. The general plasma profiles are similar to the desired target plasma level profile shown in FIG. 1.

It is to be understood, however, that the scope of the present invention is not to be limited to the specific embodiments described above. The invention may be practiced other than as particularly described and still be within the scope of the accompanying claims.

CITED LITERATURE

1. B. Lemmer, "Circadian Rhythms and Drug Delivery", J. Controlled Release, 16, 63–74 (1991)
2. B. Lemmer, "Why are so may Biological Systems Periodic?" in Pulsatile Drug Delivery: Current Applications and Future Trends, R Gurny, H E Junginger and N A Peppas, eds. (Wissenschaftliche Verlagsgesellschaft mbH Stuttgart, Germany 1993) pp.11–24
3. X. Xu and P I Lee, "Programmable Drug Delivery from an Erodible Association Polymer System", Pharm. Res. 10(8), 1144–1152 (1993)
4. A. Gazzaniga, M E Sangalli, and F Giodano, "Oral Chonotropic Drug Delivery Systems: Achievement of Time and/or Site Specificity", Eur J. Pharm. Biopharm., 40(4), 246–250 (1994)

5. A Gazzaniga, C Busetti, L Moro, M E Sangalli and F Giordano, "Time Dependent Oral Delivery Systems for Colon Targeting", S.T.P. Pharma Sciences 5(1), 83–88 (1996)
6. U Conte, L Maggi, M L Torre, P Giunchedi and A Lamanna, "Press-coated Tablets for Time programmed Release of Drugs", Biomaterials, 14(13), 1017–1023 (1993)
7. A C Shah International Patent Application WO87/00044
8. P S Walia, P Jo Mayer Stout and R Turton, "Preliminary Evaluation of an Aqueous Wax Emulsion for Controlled Release Coating",Pharm Dev Tech, 3(1), 103–113 (1998)
9. F Theeuwes, "OROS® Osmotic System Development", Drug Dev Ind Pharm 9(7), 1331–1357 (1983)
10. F Theeuwes, "Triggered Pulsed and Programmed Drug Delivery" in Novel Drug Delivery and its Therapeutic Application, L F Prescott and W S Nimmos, eds (Wiley, New York, 1989) pp.323–340
11. M McNeil, A Rashid and H Stevens, International Patent App WO90/09168
12. I R Wilding, S S Davis, M Bakhshaee, H N E Stevens, R A Sparrow and J Brennan, "Gastrointestinal Transit and Systemic Absorption of Captopril from a Pulsed Release Formulation", Pharm Res 9(5), 654–657 (1992)

What is claimed is:

1. A pharmaceutical formulation for delivery of a mixture of amphetamine base salts effective to treat ADHD in a human patient comprising:

an immediate release dosage form that provides immediate release upon oral administration to said patient;

a delayed enteric release dosage form that provides delayed release upon oral administration to said patient; and a pharmaceutically acceptable carrier;

wherein said amphetamine base salts comprise dextroamphetamine sulfate, dextroamphetamine saccharate, amphetamine aspartate monohydrate and amphetamine sulfate;

wherein said pharmaceutical formulation is sufficient to maintain an effective level of amphetamine base salts in the patient over the course of at least 8 hours without further administration of amphetamine base salt, and the peak plasma concentration of amphetamine base salts reached after release of said delayed enteric release dosage form exceeds the peak plasma concentration previously reached after release of said immediate release dosage form; and wherein said pharmaceutical formulation, when containing about a total dose of 20 mg, will produce in a human individual a plasma concentration versus time curve (ng/ml versus hours) having an area under the curve (AUC) of about 467 to about 714 ng hr/ml.

2. A formulation of claim 1 wherein said plasma concentration curve has a maximum concentration ($C_{max}$) of about 22.5 to about 40 ng/ml for about a total dose of 20 mg.

3. A formulation of claim 2 wherein the time after said oral administration to reach said $C_{max}$ value is about 7 to about 10 hours.

4. A formulation of claim 1 wherein the time after said oral administration to reach maximum concentration of said plasma concentration curve is about 7 to about 10 hours.

5. A formulation of claim 2, 3 or 4 wherein said AUC is about 714 ng hr/ml.

6. A formulation of claim 3 wherein said AUC is about 714 ng hr/ml, the time after said oral administration to reach said $C_{max}$ value is about 7 hours and $C_{max}$ is about 40 ng/ml.

7. A formulation of claim 2 wherein $C_{max}$ is about 40 ng/ml.

8. A formulation of claim 3 or 4 wherein said time is about 7 hours.

9. A formulation of one of claims 1–4, 6 or 7 wherein said salts are contained in about equal amounts within each of said dosage forms.

10. A formulation of one of claims 1–4, 6 or 7 wherein said delayed enteric release dosage form comprises a coating of a thickness of [at least] *greater than* 20 μm which comprises dried about 30% (dry substance) aqueous dispersion of an anionic copolymer based on methacrylic acid and acrylic acid ethyl ester, said coating being soluble at a pH of about 5.5 upwards.

11. A formulation of claim 10 wherein said thickness is at least 25 μm.

12. A pharmaceutical formulation for delivery of a mixture of amphetamine base salts effective to treat ADHD in a human patient comprising:

an immediate release dosage form that provides immediate release upon oral administration to said patient;

a delayed enteric release dosage form that provides delayed release upon oral administration to said patient, wherein said enteric release dosage form comprises a coating of a thickness of [at least] *greater than* 20 μm which comprises dried aqueous dispersion of an anionic copolymer based on methacrylic acid and acrylic acid ethyl ester, said coating being soluble at a pH of about 5.5 upwards; and a pharmaceutically acceptable carrier;

wherein said amphetamine base salts comprise dextroamphetamine sulfate, dextroamphetamine saccharate, amphetamine aspartate monohydrate and amphetamine sulfate;

wherein said pharmaceutical formulation is sufficient to maintain an effective level of amphetamine base salts in the patient over the course of at least 8 hours without further administration of amphetamine base salt, and the peak plasma concentration of amphetamine base salts reached after release of said delayed enteric release dosage form exceeds the peak plasma concentration of said salts previously reached after release of said immediate release dosage form.

13. A formulation of claim 12 wherein said thickness is at least 25 μm.

14. A formulation of claim 12, wherein said dried aqueous dispersion of an anionic copolymer is a dried about 30% (dry substance) aqueous dispersion of an anionic copolymer.

15. A formulation of claim 1 formulated for a total dose of 20 mg.

16. A formulation of claim 2 formulated for a total dose of 20 mg.

17. A formulation of claim 1 formulated for a total dose different from about 20 mg and having an AUC proportional to said 20 mg AUC.

18. A formulation of claim 2 formulated for a total dose different from about 20 mg and having a $C_{max}$ proportional to said 20 mg $C_{max}$.

*19. The pharmaceutical formulation of claim 1, wherein the delayed release is pH independent.*

*20. The pharmaceutical formulation of claim 1, which further comprises a protective coating layer.*

* * * * *

UNITED STATES PATENT AND TRADEMARK OFFICE

CERTIFICATE OF CORRECTION

PATENT NO. : RE41,148 E
APPLICATION NO. : 11/091010
DATED : February 23, 2010
INVENTOR(S) : Beth A. Burnside et al.

It is certified that error appears in the above-identified patent and that said Letters Patent is hereby corrected as shown below:

Title page, item (73) should read as follows:

(73) Assignee: Shire LLC, Florence, KY (US)

Signed and Sealed this
Eighth Day of February, 2011

David J. Kappos

David J. Kappos
*Director of the United States Patent and Trademark Office*